(12) United States Patent
Fukumoto et al.

(10) Patent No.: US 7,223,773 B2
(45) Date of Patent: May 29, 2007

(54) 4-OXOQUINOLIZINE ANTIBACTERIAL AGENT HAVING 2-PYRIDONE SKELETON AS PARTIAL STRUCTURE

(75) Inventors: Ryoichi Fukumoto, Hachioji (JP); Yoshimi Niwano, Osakasayama (JP); Hiroyuki Kusakabe, Chiba (JP); Chong Chu, Chiba (JP); Hiroaki Kimura, Tokyo (JP); Koh Nagasawa, Tokyo (JP); Satoshi Yanagihara, Kawasaki (JP); Chisato Hirosawa, Tokyo (JP); Seiji Ishiduka, Hachioji (JP)

(73) Assignee: Salo Pharmaceutical Co., Ltd., Tokyo (JP)

( * ) Notice: Subject to any disclaimer, the term of this patent is extended or adjusted under 35 U.S.C. 154(b) by 223 days.

(21) Appl. No.: 10/809,874

(22) Filed: Mar. 26, 2004

(65) Prior Publication Data

US 2004/0229903 A1    Nov. 18, 2004

Related U.S. Application Data

(63) Continuation of application No. PCT/JP02/10103, filed on Sep. 27, 2002.

(30) Foreign Application Priority Data

Sep. 28, 2001 (JP) .............................. 2001-299088
Oct. 24, 2001 (JP) .............................. 2001-326133

(51) Int. Cl.
*A61K 31/44* (2006.01)
*C07D 455/02* (2006.01)

(52) U.S. Cl. ....................... 514/306; 546/138
(58) Field of Classification Search ................ 514/299, 514/306; 546/141, 138
See application file for complete search history.

(56) References Cited

FOREIGN PATENT DOCUMENTS

WO       WO9639407       * 12/1996

* cited by examiner

*Primary Examiner*—Bernard Dentz
*Assistant Examiner*—Binta Robinson
(74) *Attorney, Agent, or Firm*—Nixon Peabody LLP; Donald R. Studebaker

(57) ABSTRACT

The present invention provides a 4-oxoquinolizine antibacterial agent having a 2-pyridone skeleton as a partial structure and also having a strong antibacterial effect on gram-positive bacteria, gram-negative bacteria or anaerobic bacteria. The compound having the following formula (I) or a pharmaceutically acceptable salt thereof:

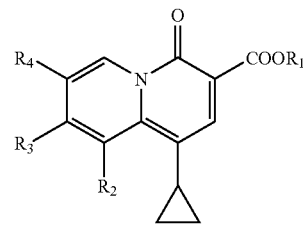

(I)

wherein:
$R_1$ represents hydrogen atom or a carboxyl-protecting group,
$R_2$ represents hydrogen atom, a halogen atom, a lower alkyl group, a lower alkoxyl group or hydroxyl group,
$R_3$ represents phenyl group or an aromatic substituent selected from the group consisting of 5-membered and 6-membered heterocyclic groups and $R_3$ has a substituent selected from the group consisting of a hydrogen atom, a lower alkyl group, a lower alkoxyl group, a nitro group, a cyano group, an amino group, an acyl group, a carbamoyl group and a ureido group, and
$R_4$ represents a hydrogen atom or a halogen atom.

12 Claims, 5 Drawing Sheets

Reaction scheme (1)

Reaction scheme (1)

Reaction scheme (2)

Reaction scheme (3)

Reaction scheme (4)

Reaction scheme (5)

Reaction scheme (6)

Reaction scheme (7)

4-OXOQUINOLIZINE ANTIBACTERIAL AGENT HAVING 2-PYRIDONE SKELETON AS PARTIAL STRUCTURE

This application is a continuation of international application number PCT/JP02/1013, filed Sep. 27, 2002. (status, abandoned, pending, etc.)

TECHNICAL FIELD

The present invention relates to a new synthetic antibacterial agent having a strong antibacterial effect on gram-positive bacteria, gram-negative bacteria or anaerobic bacteria.

BACKGROUND OF THE INVENTION

Synthetic quinolone antibacterial agents having a quinoloine skeleton have so far been widely studied.

For example, it was found that the antibacterial activity of a synthetic antibacterial agent is remarkably increased by introducing a fluorine group into the 6-position of quinolone skeleton thereof. Fluorine atom at the 6-position is considered to be a structural characteristic indispensable for synthetic quinolone antibacterial agents of the second generation or, in other words, new synthetic quinolone antibacterial agents. Pyrrolidine ring, piperazine ring or the like introduced through C—N bond is also considered to be an indispensable structural characteristic because a substituent at the 7-position of the quinolone structure exerts a considerable influence on the antibacterial activity, internal dynamics and toxicity.

Synthetic quinolone antibacterial agents have so far clinically widely been used as excellent agents having a high antibacterial activity. However, recently, it has become possible to separate many multiple drug-resistant bacteria also resistant to the synthetic quinolone antibacterial agents. However, fluorine atom at the 6-position of the quinolone skeleton and the substituent introduced through C—N bond at the 7-position of the quinolone skeleton, which are indispensable in the structure of the new synthetic quinolone antibacterial agents, are considered to be the causes for the side effects of the new synthetic quinolone antibacterial agents on the central nervous system. Those problems of the multiple drug-resistant bacteria and the side effects are mostly due to the structural characteristics of the new synthetic quinolone antibacterial agents. Under these circumstances, it is demanded to develop a drug having a skeleton different from the quinolone skeleton of the current antimicrobial agents and also a high antimicrobial activity.

DISCLOSURE OF THE INVENTION

After intensive investigations made for the purpose of solving the above-described problems in this field until now, the inventors have found that new compounds represented by formula (I) given below have a wide antibacterial spectrum and a high antibacterial activity on quinolone-resistant bacteria, while they do not have a structure in which the substituent is introduced through C—N bond at the 7-position of the new quinolone skeleton as the mother nucleus. The present invention has been completed on the basis of this finding. The synthetic 4-oxoquinolizine antibacterial agents of the present invention are new compounds free from the structural characteristics of the synthetic new quinolone antibacterial agents and free from the extension of the prior techniques.

In particular, the compounds of the present invention have a monocyclic substituent bonded through C—C bond. The compounds having such a structure have not yet been developed in the art.

Namely, the present invention relates to a compound having the following formula (1) or a salt thereof:

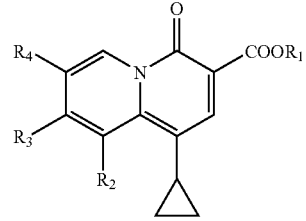

(I)

wherein:
$R_1$ represents a hydrogen atom or a carboxyl-protecting group,
$R_2$ represents a hydrogen atom, a halogen atom, a lower alkyl group, a lower alkoxyl group or a hydroxyl group,
$R_3$ represents a phenyl group or an aromatic group selected from the group consisting of 5-membered or 6-membered heterocyclic groups and $R_3$ has a substituent selected from the group consisting of a hydrogen atom, a lower alkyl group, a lower alkoxyl group, a nitro group, a cyano group, an amino group, an acyl group, a carbamoyl group, a ureido group, a halogen atom, a hydroxyl group and a carboxyl group, and
$R_4$ represents a hydrogen atom or a halogen atom.

MODE FOR CARRYING OUT THE INVENTION

Figure 1:
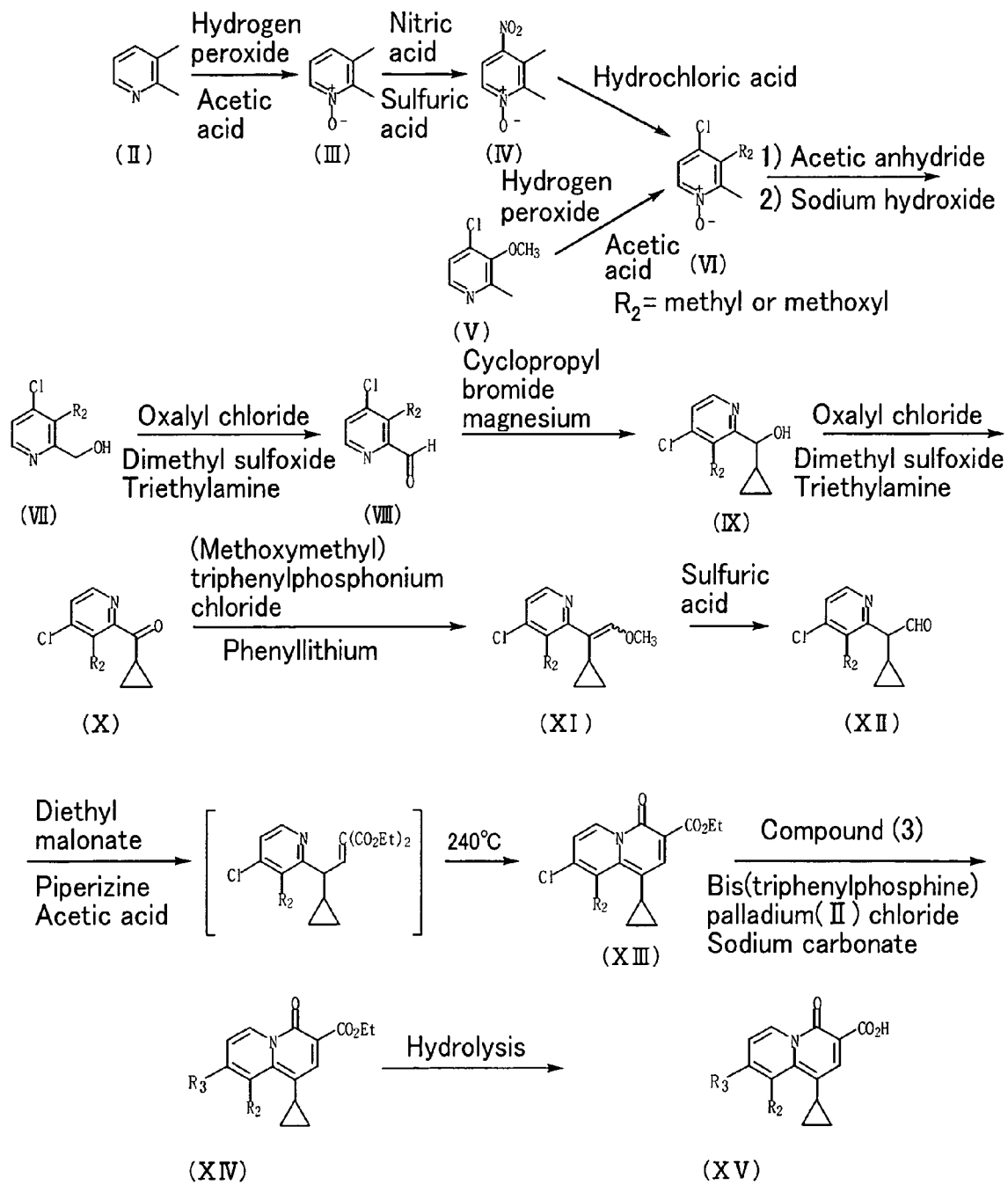
FIG. 1 shows reaction scheme 1.

The present invention will be described in detail below.
In formula (I), $R_1$ represents a hydrogen atom or a carboxyl-protecting group. The groups protecting carboxyl group (carboxyl-protecting groups) are, for example, methyl group, ethyl group, n-propyl group, isopropyl group, n-butyl group, isobutyl group, sec-butyl group and tert-butyl group.

$R_2$ represents a hydrogen atom, a halogen atom, a lower alkyl group, a lower alkoxyl group or a hydroxyl group.

The halogen atoms are fluorine atom, chlorine atom, bromine atom or iodine atom.

The alkyl groups are usually saturated alkyl groups having 1 to 20 carbon atoms, preferably 1 to 15 carbon atoms and more preferably 1 to 10 carbon atoms. The alkyl groups may be either linear or branched. Concretely, the lower alkyl groups have, for example, about 1 to 8 carbon atoms, preferably about 1 to 5 carbon atoms.

The alkyl groups include lower alkyl groups such as methyl group, ethyl group, n-propyl group, isopropyl group, n-butyl group, isobutyl group, sec-butyl group, tert-butyl group and pentyl group, and also decyl group, dodecyl group, tridecyl group and undecyl group.

The alkoxyl group comprises an alkyl group and oxygen atom bonded therewith. The alkyl groups constituting the alkoxyl groups are the same as those described above. The alkoxyl groups are linear or branched lower alkoxyl groups such as methoxyl group, ethoxyl group, n-propoxyl group, isopropoxyl group, n-butoxyl group, isobutoxyl group, sec-butoxyl group, tert-butoxyl group and pentyloxyl group.

$R_3$ represents a phenyl group or a 5-membered or 6-membered aromatic heterocyclic group. The 5-membered or 6-membered heterocyclic groups are, for example, thiophenyl group, pyridyl group, furyl group and pyrrolyl group. The phenyl group and aromatic group having a 5-membered or 6-membered ring have a substituent selected from the group consisting of a hydrogen atom, a lower alkyl group, a lower alkoxyl group, a nitro group, a cyano group, an amino group, an acyl group, a carbamoyl group, a ureido group, a halogen atom, a hydroxyl group and a carboxyl group.

The phenyl group and the 5-membered or 6-membered heterocyclic groups may have two or more substituents. They are, for example, a phenyl group in which two hydrogen atoms are replaced with amino groups or with one amino group and one methyl group.

The lower alkyl groups and lower alkoxyl groups as the substituents are the same as those defined above and, if necessary, they may be substituted with amino group, oxygen atom, a halogen atom, hydroxyl group, hydroxyimino group, piperazyl group or the like. Those amino groups may also be replaced with a lower alkyl group, hydroxyl group, cyclopropyl group or the like.

The amino group as the substituent may be, if necessary, substituted with an amino group-protecting group, such as a lower alkyl group, an acyl group, butoxycarbonyl group or trityl group to form an alkylamino group or the like. The alkylamino groups are, for example, methylamino group, dimethylamino group, ethylamino group, n-propylamino group, isopropylamino group, n-butylamino group, isobutylamino group, sec-butylamino group and tert-butylamino group. The alkylamino groups and others may be further substituted with a cyclic substituent such as tetrahydropyran.

Preferred acyl groups as the substituents are formyl group, acetyl group, etc.

The hydroxyl group in hydroxyimino group may be protected with a hydroxyl-protecting group such as an alkoxyl group.

$R_4$ represents a hydrogen atom or a halogen atom. The halogen atom is fluorine, chlorine, bromine or iodine atom.

The salts of the compounds of the above formula (I) are those with inorganic carboxylic acids such as hydrochloric acid, sulfuric acid and phosphoric acid, organic carboxylic acids such as tartaric acid, formic acid, acetic acid, citric acid, fumaric acid and lactic acid, sulfonic acids such as methanesulfonic acid, benzenesulfonic acid, p-toluenesulfonic acid and mesitylenesulfonic acid, alkali metals such as sodium and potassium, alkaline earth metals such as calcium and magnesium, and nitrogen-containing organic bases such as ammonium.

The compounds of formula (I) and salts thereof include salvation products thereof, hydrates thereof and crystals thereof in various forms.

The compounds of formula (I) also include stereoisomers thereof.

Concrete examples of the compounds of the present invention are those described in Examples given below. The compounds of the present invention are preferably those described in Examples including esters thereof. However, they are not limited to those described in Examples.

From the viewpoint of the physical properties of the compounds of the present invention, $R_3$ in formula (I) is preferably a substituent having nitrogen atom. When $R_3$ has a nitrogen atom, the compound is highly soluble in water.

The description will be made on the processes for synthesizing the compounds represented by formula (I) (hereinafter referred to as "compounds of the present invention").

The compounds of the present invention can be synthesized by a known process. For example, the compounds of the present invention can be synthesized by a synthesis route shown in reaction scheme 1 in FIG. 1.

In reaction scheme (1), $R_2$ and $R_3$ are as defined above.

Concretely, a compound of formula (VI) in reaction scheme (1) can be synthesized from compound (II) (2,3-dimethylpyridine) and compound (V) (4-chloro-3-methoxy-2-methylpyridine) commercially available on the market.

Namely, compound (III) can be obtained by dissolving compound (II) in acetic acid, adding an oxidizing agent such as hydrogen peroxide and heating the resultant mixture at, for example, 70 to 100° C. for 5 to 24 hours.

Then, compound (III) is nitrated to obtain compound (IV). The nitrating agents usable herein are, for example, concentrated nitric acid, a mixture of nitric acid and sulfuric acid, sulfuric acid, nitrates (such as potassium nitrate and sodium nitrate) and nitric anhydride.

Thereafter, compound (IV) is dissolved in concentrated hydrochloric acid and the obtained solution is heated at, for example, 120 to 160° C. in a sealed tube for 5 to 12 hours to obtain the compound (VI, $R_2$ is methyl group).

Compound (V) is dissolved in acetic acid and then oxidized with hydrogen peroxide in the same manner as that described above to obtain a compound (VI, $R_2$ is methoxyl group).

Compound (VI) is dissolved in acetic anhydride. The obtained solution is heated to, for example, 70 to 110° C. for 0.5 to 5 hours. A base is added to the obtained residue and then the reaction is conducted at, for example, 50 to 90° C. for 1 to 5 hours to obtain compound (VII). The bases usable herein are, for example, sodium hydroxide, potassium hydroxide and lithium hydroxide.

Compound (VII) is then oxidized to obtain compound (VIII). The oxidizing agents usable herein are, for example, dichromic acid/sulfuric acid, chromium (VI) oxide/pyridine complex, dimethyl sulfoxide/oxalyl chloride and dimethyl sulfoxide/trifluoroacetic anhydride.

Compound (VIII) is then reacted with a Grignard reagent prepared from cyclopropyl bromide and magnesium to obtain compound (IX). The reaction is conducted at, for example, 0 to 50° C. for 1 to 15 hours.

Compound (IX) is oxidized in the same manner as that described above to obtain compound (X).

Compound (X) is then reacted with a Wittig reagent prepared from (methoxymethyl) triphenylphosphonium chloride and a base to obtain compound (XI).

The bases usable herein are, for example, phenyllithium, n-butyllithium and lithium bis(trimethylsilyl)amide. The reaction is conducted at, for example, 0 to 50° C. for 1 to 5 hours.

Compound (XI) is hydrolyzed in the presence of an acid to obtain compound (XII). The acids usable herein are, for example, hydrochloric acid, hydrobromic acid, sulfuric acid and acetic acid. The reaction is conducted at, for example, 40 to 80° C. for 2 to 5 hours.

Compound (XII) is then subjected to Knoevenagel condensation reaction with diethyl malonate in the presence of an amine as a catalyst to obtain an unsaturated carboxylic acid diester as an intermediate. The amines usable herein are, for example, piperidine, pyridine and diethylamine. The reaction is conducted at, for example, 50 to 100° C. for 2 to 5 hours. This intermediate is not purified and it is dissolved in a solvent having a high boiling point such as diphenyl ether or Dowtherm A (a mixture of diphenyl ether and biphenyl) and then heated at, for example, 200 to 250° C. for 0.5 to 2 hours to obtain compound (XIII).

Compound (XIII) is then reacted with compound (3) in the presence of a catalyst such as bis(triphenylphosphine) palladium (II) chloride in a solvent such as toluene to obtain compound (XIV) of the present invention.

Compounds (3) used herein are, for example, compounds of the following formula:

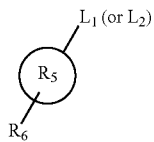

wherein $R_5$ is selected from the group consisting of a phenyl group and 5- or 6-membered heterocyclic groups, $R_6$ is selected from the group consisting of a hydrogen atom, a lower alkyl group, a lower alkoxyl group, a nitro group, a cyano group, an amino group, a formyl group, a carbamoyl group, a ureido group, a halogen atom, a hydroxyl group and a carboxyl group, $L_1$ represents, for example, tin (alkyl group)$_3$, and $L_2$ represents, for example, boron (lower alkoxyl group)$_2$.

Compound (XIV) thus obtained is then hydrolyzed by an ordinary method to obtain compound (XV) of the present invention.

Figure 2:
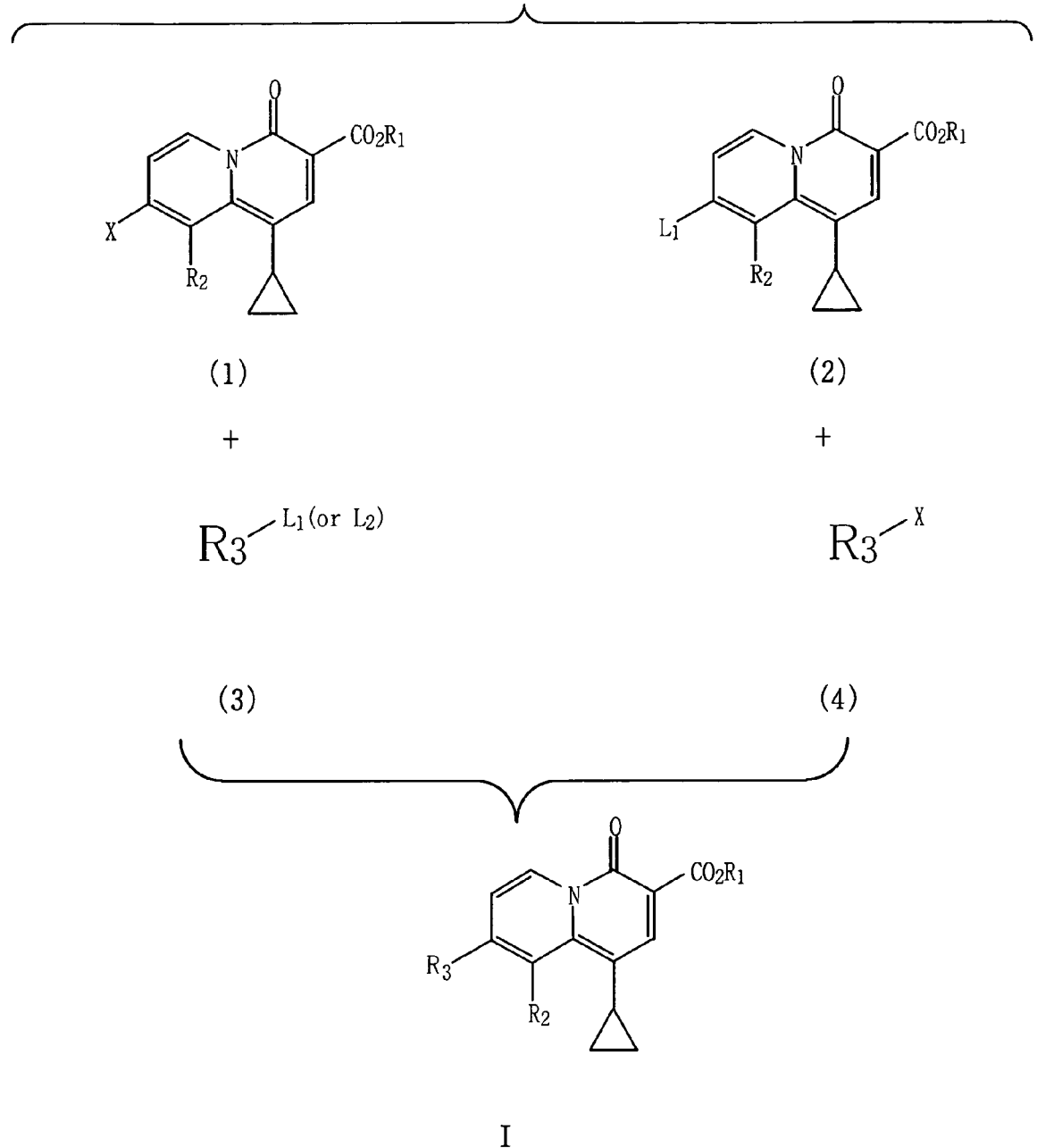
FIG. 2 shows reaction scheme 2.

The compounds of formula (I) can also be synthesized according to reaction scheme (2) shown in FIG. 2.

In reaction scheme (2), $R_1$, $R_2$ and $R_3$ are as defined above, $L_1$ represents tin(alkyl group)$_3$, $L_2$ represents boron (lower alkoxyl group)$_2$ and X represents a halogen atom.

In reaction scheme (2), the intended compound can be obtained by coupling a compound of formula (1) with an organotin compound of formula (3) in the presence of a palladium complex as the catalyst, or by coupling a compound of formula (4) with an organotin compound of formula (2).

The solvent used for this reaction is not particularly limited so far as it does not exert a bad influence on the reaction. The solvents are, for example, aromatic hydrocarbons such as benzene, toluene and xylene; ethers such as dioxane, tetrahydrofuran, anisole, diethylene glycol diethyl ether and dimethyl cellosolve; nitriles such as acetonitrile; amides such as N,N-dimethylformamide and N,N-dimethylacetamide; and sulfoxides such as dimethyl sulfoxide. The solvents are usable either alone or in the form of a mixture of two or more of them.

The palladium complex catalysts usable for this reaction are, for example, PdCl$_2$(PPh$_3$)$_2$, Pd(PPh$_3$)$_4$, PdCl$_2$(P(O-tolyl)$_3$)$_2$, PdCl$_2$+2P(OEt)$_3$ and PdCl$_2$(PhCN)$_2$ wherein Ph represents a phenyl group and Et represents an ethyl group.

The organotin compound of formula (3) is used in an amount of at least equimolar to the compound of formula (1), preferably 1.0 to 2.0 mols per mol of the latter.

The coupling reaction is usually conducted at 50 to 170° C. in an inert gas (such as argon or nitrogen) atmosphere for 1 minute to 24 hours.

In another method, a compound of formula (1) is coupled with an organoboron compound of formula (3) in the presence of the palladium complex catalyst described above in the presence or absence of a base.

The solvent used for this reaction is not particularly limited so far as it does not exert a bad influence on the reaction. The solvents are, for example, water; alcohols such as methanol, ethanol and propanol; aromatic hydrocarbons such as benzene, toluene and xylene; halogenated hydrocarbons such as methylene chloride, chloroform and dichloroethane; ethers such as dioxane, tetrahydrofuran, anisole, diethylene glycol diethyl ether and dimethyl cellosolve; esters such as ethyl acetate and butyl acetate; ketones such as acetone and methyl ethyl ketone; nitriles such as acetonitrile; amides such as N,N-dimethylformamide and N,N-dimethylacetamide; and sulfoxides such as dimethyl sulfoxide. The solvents are usable either alone or in the form of a mixture of two or more of them. The bases usable for the reaction are, for example, sodium hydrogencarbonate, sodium carbonate, potassium carbonate and triethylamine.

The organoboron compound of formula (3) is used in an amount of at least equimolar to the compound of formula (1), preferably 1.0 to 1.50 mols per mol of the latter.

The coupling reaction is usually conducted at 50 to 170° C. in an inert gas (such as argon or nitrogen) atmosphere for 1 minute to 24 hours.

In the compounds of formula (I) thus obtained, $R_6$ shown above can be varied within the above-described range by various reactions. It is also possible that $R_6$ is varied within the range and then the coupling reaction is conducted.

Figure 3:
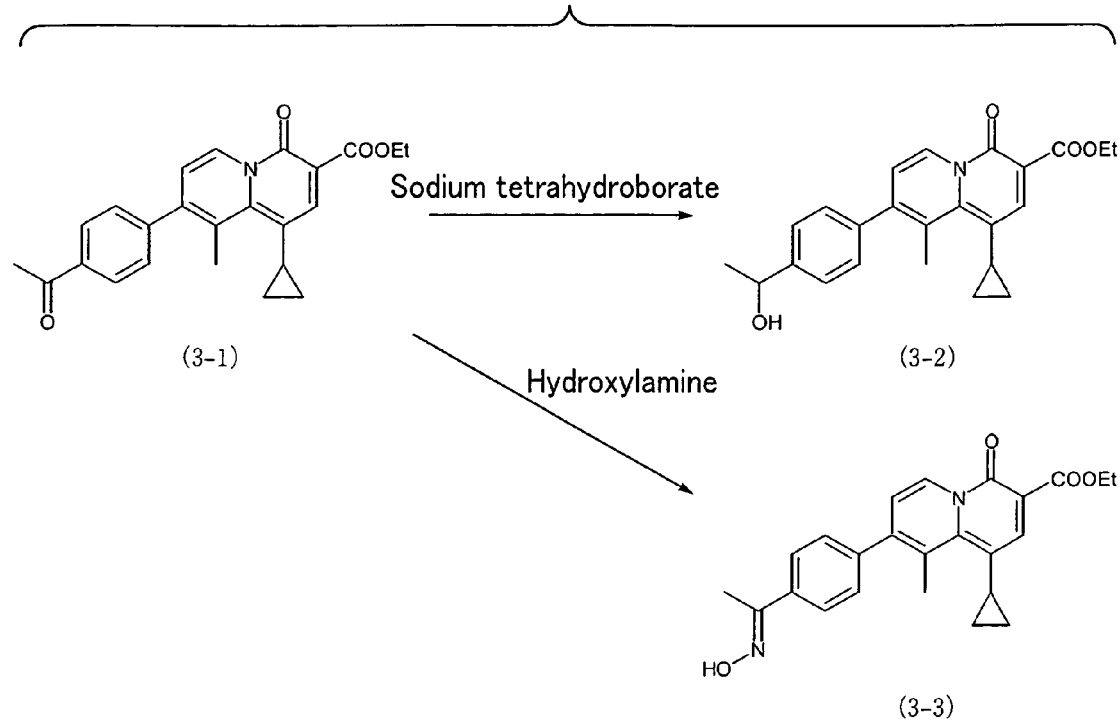
FIG. 3 shows reaction scheme 3.

For example, compound (3-1) can be reduced with sodium tetrahydroborate or the like to form compound (3-2) as shown in reaction scheme (3) in FIG. 3.

The reducing agents usable for this purpose are, for example, sodium tetrahydroborate, potassium tetrahydroborate and lithium aluminum hydride. The solvent used for this reaction is not particularly limited so far as it does not exert a bad influence on the reaction. The solvents are, for example, water; alcohols such as methanol, ethanol and propanol; and ethers such as dioxane, tetrahydrofuran, anisole, diethylene glycol diethyl ether and dimethyl cellosolve. The solvents are usable either alone or in the form of a mixture of two or more of them. The reaction is conducted at −50 to 70° C. for, for example, 1 to 60 hours.

Compound (3-1) can be converted into compound (3-3) by, for example, the reaction with hydroxylamine. The reagents usable herein are, for example, hydroxylamine, O-methylhydroxylamine and O-ethylhydroxylamine. The solvent used for this reaction is not particularly limited so far as it does not exert a bad influence on the reaction. The solvents are, for example, alcohols such as methanol, ethanol and propanol; ethers such as dioxane, tetrahydrofuran, anisole, diethylene glycol diethyl ether and dimethyl cellosolve; and aromatic hydrocarbons such as benzene, toluene and xylene. The solvents are usable either alone or in the form of a mixture of two or more of them. The reaction is usually conducted at 50 to 160° C. for 1 minute to 20 hours.

Figure 4:
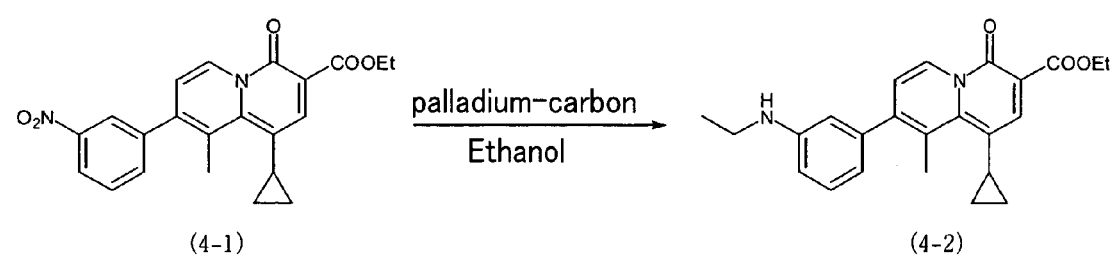
FIG. 4 shows reaction scheme 4.

As shown in reaction scheme (4) in FIG. 4, compound (4-1) can be converted into compound (4-2) by reducing it with, for example, palladium carbon in ethanol solvent in hydrogen atmosphere.

The catalysts usable for this reaction are, for example, palladium carbon, palladium complexes and Raney nickel. Hydrogen pressure may be either atmospheric pressure or elevated pressure. The reaction is conducted at −5 to 70° C. for, for example, 1 to 50 hours. The solvents usable for the reaction are alcohols such as methanol, ethanol and propanol.

Figure 5:
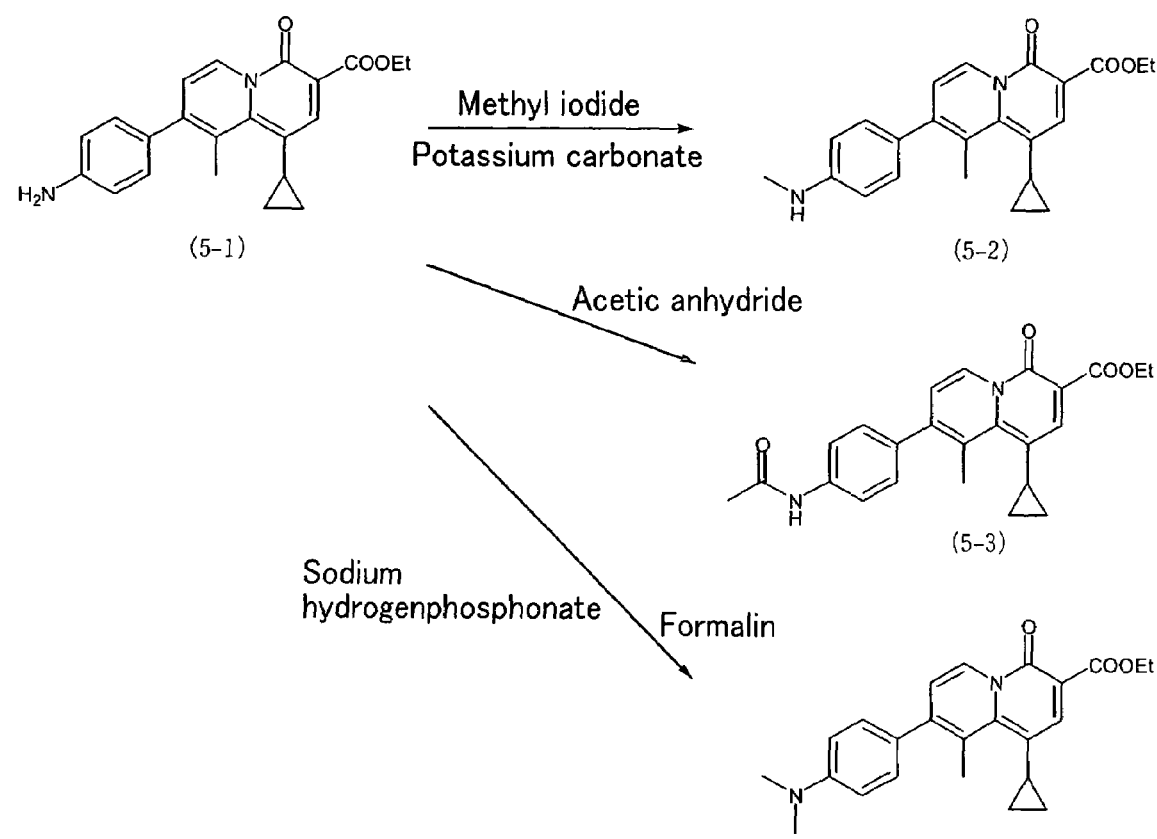
FIG. 5 shows reaction scheme 5.

As shown in reaction scheme (5) in FIG. 5, compound (5-1) can be converted into compound (5-2) by reacting it with, for example, methyl iodide in the presence or absence of a base.

The bases are, for example, potassium carbonate, sodium hydroxide, ammonia, triethylamine and pyridine.

The reagents usable herein are, for example, alkyl halides such as methyl iodide, ethyl iodide and 2-(2-bromoethoxy) tetrahydro-2H-pyran; sulfonic acid esters such as methyl methanesulfonate and ethyl methanesulfonate; and sulfuric acid esters such as dimethyl sulfate and diethyl sulfate. The solvent used for this reaction is not particularly limited so far as it does not exert a bad influence on the reaction. The solvents are, for example, ethers such as dioxane, tetrahydrofuran, anisole, diethylene glycol diethyl ether and dimethyl cellosolve; aromatic hydrocarbons such as benzene, toluene and xylene; ketones such as acetone and methyl ethyl ketone; nitriles such as acetonitrile; amides such as N,N-dimethylformamide and N,N-dimethylacetamide; and sulfoxides such as dimethyl sulfoxide. The solvents are usable either alone or in the form of a mixture of two or more of them. The reaction is conducted at 30 to 180° C. for 1 to 60 hours. For improving the reactivity, sodium iodide, potassium iodide or the like is usable in a suitable amount.

Compound (5-1) can be converted into compound (5-3) by, for example, reacting it with acetic anhydride or the like in the presence or absence of a base. The reagents usable herein are, for example, acid anhydrides such as acetic anhydride and propionic anhydride; and acid halides such as acetyl chloride and propionyl chloride. The solvent used for this reaction is not particularly limited so far as it does not exert a bad influence on the reaction. The solvents are, for example, aromatic hydrocarbons such as benzene, toluene and xylene; aromatic amines such as pyridine; and halogenated hydrocarbons such as methylene chloride, chloroform and dichloroethane. The solvents are usable either alone or in the form of a mixture of two or more of them. The reaction is conducted at 30 to 100° C. for 1 to 20 hours.

Compound (5-1) can be converted into compound (5-4) by reacting it with, for example, an aldehyde such as formaldehyde, acetaldehyde or propionaldehyde; or a ketone such as acetone or methyl ethyl ketone in the presence of a reducing agent. The reducing agents usable herein are, for example, sodium hydrogenphosphonate, potassium hydrogenphosphonate, sodium tetrahydroborate, potassium tetrahydroborate and sodium cyanotrihydroborate. The solvent used for this reaction is not particularly limited so far as it does not exert a bad influence on the reaction. The solvents are, for example, water; and ethers such as dioxane, tetrahydrofuran, anisole, diethylene glycol diethyl ether and dimethyl cellosolve. The solvents are usable either alone or in the form of a mixture of two or more of them. The reaction is conducted at 30 to 180° C. for 1 to 50 hours.

Figure 6:
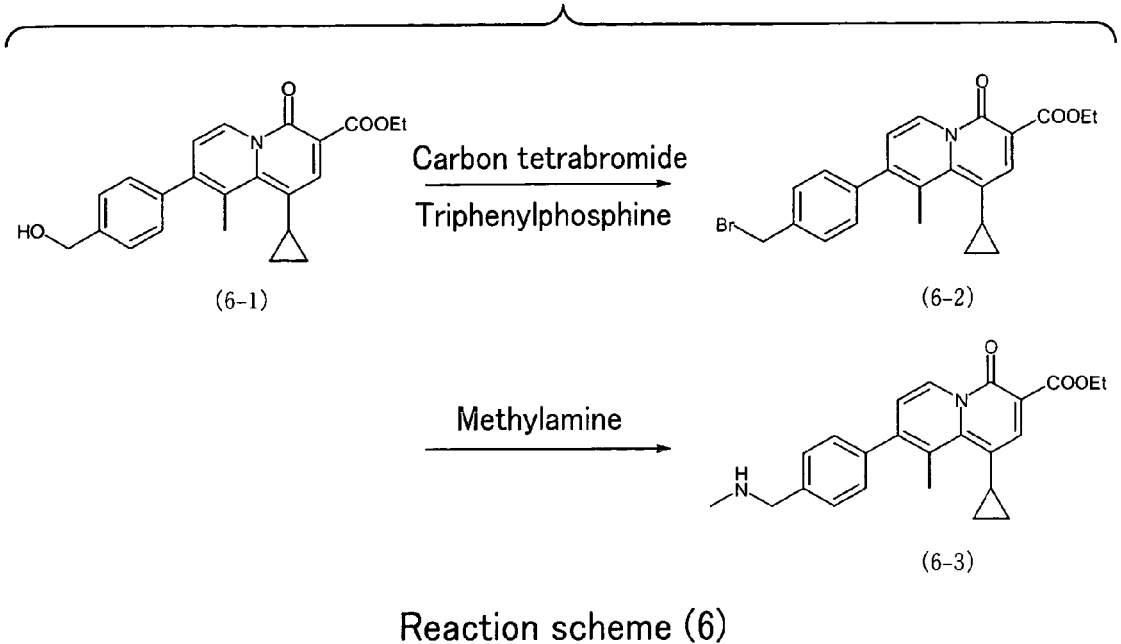
FIG. 6 shows reaction scheme 6.

As shown in reaction scheme (6) in FIG. 6, compound (6-1) can be converted into compound (6-2) having a leaving group by the halogenation or the like.

The leaving groups are, for example, halogens such as chlorine, bromine and iodine; and sulfonic acid ester groups such as methanesulfonyl group and p-toluenesulfonyl group. The halogenating agents are, for example, bromine, hydrogen bromide, thionyl chloride, phosphorus tribromide and carbon tetrabromide/triphenylphosphine. The sulfonic acid esterifying agents are, for example, methanesulfonyl chloride and p-toluenesulfonyl chloride. The solvent used for this reaction is not particularly limited so far as it does not exert a bad influence on the reaction. The solvents are, for example, water; aromatic hydrocarbons such as benzene, toluene and xylene; aromatic amines such as pyridine; halogenated hydrocarbons such as methylene chloride, chloroform and dichloroethane; ethers such as dioxane, tetrahydrofuran, anisole, diethylene glycol diethyl ether and dimethyl cellosolve. The solvents are usable either alone or in the form of a mixture of two or more of them. The reaction is conducted at −10 to 120° C. for 1 to 30 hours.

Compound (6-2) can be converted into compound (6-3) by reacting it with, for example, methylamine in the presence or absence of a base (such as potassium carbonate, sodium hydroxide, ammonia or triethylamine). The reagents usable herein are, for example, amines such as ammonia, methylamine, ethylamine and cyclopropylamine; alcohols such as methanol, ethanol and cyclopropanol; and thiols such as methanethiol, ethanethiol and cyclopropanethiol. The solvent used for this reaction is not particularly limited so far as it does not exert a bad influence on the reaction. The solvents are, for example, aromatic hydrocarbons such as benzene, toluene and xylene; aromatic amines such as pyridine; ethers such as dioxane, tetrahydrofuran, anisole, diethylene glycol diethyl ether and dimethyl cellosolve; ketones such as acetone and methyl ethyl ketone; nitrites such as acetonitrile; amides such as N,N-dimethylformamide and N,N-dimethylacetamide; and sulfoxides such as dimethyl sulfoxide. The solvents are usable either alone or in the form of a mixture of two or more of them. The reaction is conducted at −5 to 180° C. for 1 to 30 hours.

Figure 7:
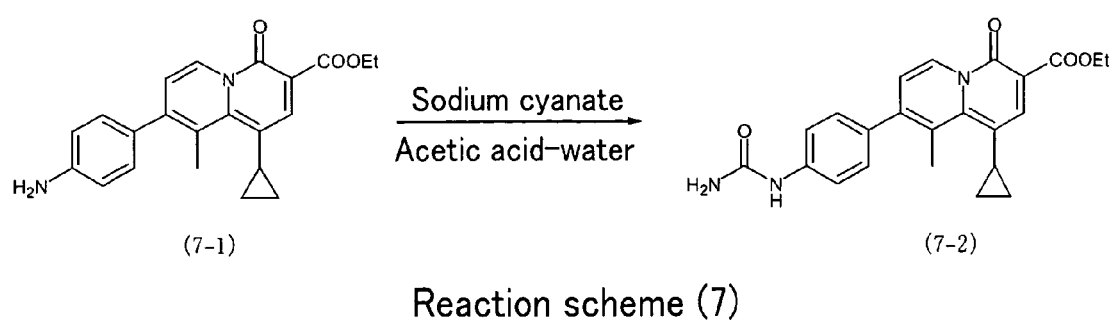
FIG. 7 shows reaction scheme 7.

As shown in reaction scheme (7) in FIG. 7, compound (7-1) can be converted into compound (7-2) by reacting it with, for example, sodium cyanate.

The reagents usable herein are, for example, cyanic acid, sodium cyanate and potassium cyanate. The solvent used for this reaction is not particularly limited so far as it does not exert a bad influence on the reaction. The solvents are, for example, water; mineral acids such as hydrochloric acid and hydrobromic acid; and organic acids such as acetic acid and propionic acid. The solvents are usable either alone or in the form of a mixture of two or more of them. The reaction is conducted at 0 to 100° C. for 1 to 30 hours.

An example of the compounds of formula (I) wherein $R_4$ represents fluorine atom is ethyl 8-chloro-1-cyclopropyl-7-fluoro-9-methyl-4-oxo-4H-quinolizine-3-carboxylate. This compound can be easily synthesized by a method described in Heterocycles, Vol. 51, No. 6, 1999, p. 1345 or J. Med. Chem. 1996, 39, 3070–3088. As for $R_3$, compounds having a desired $R_3$ of the present invention can be synthesized by a method similar to that described above.

The structural formula of ethyl 8-chloro-1-cyclopropyl-7-fluoro-9-methyl-4-oxo-4H-quinolizine-3-carboxylate is as follows:

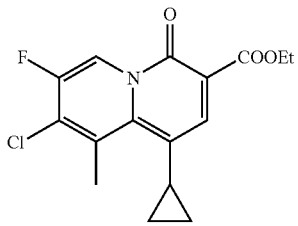

EXAMPLES

The following Examples will further illustrate the present invention, which by no means limit the scope of the present invention.

Example 1

92.7 mg of ethyl 8-chloro-1-cyclopropyl-9-methyl-4-oxo-4H-quinolizine-3-carboxylate was suspended in 1 ml of toluene. 0.5 ml of ethanol, 0.5 ml of 2 M aqueous sodium carbonate solution, 50 mg of 3-aminophenylboronic acid hydrochloride and 10 mg of bis(triphenylphosphine) palladium (II) chloride were added to the obtained suspension, and they were heated under reflux in argon atmosphere for 3 hours. Ethyl acetate was added to the reaction mixture. The organic layer was taken, washed with water and dried over anhydrous sodium sulfate. The solvent was evaporated under reduced pressure. The resultant residue was purified by the silica gel column chromatography (eluent: chloroform/ethyl acetate=4/1) to obtain 50.6 mg of ethyl 8-(3-aminophenyl)-1-cyclopropyl-9-methyl-4-oxo-4H-quinolizine-3-carboxylate.

$^1$H-NMR(CDCl$_3$) δ: 0.77–0.78(2H, m), 1.01–1.03(2H, m), 1.43(3H, t, J=7.1 Hz), 2.35(1H, m), 2.82(3H, s), 3.88 (2H, brs), 4.43(2H, q, J=7.1 Hz), 6.67–7.29(5H, m), 8.40 (1H, s), 9.44(1H, d, J=7.1 Hz)

Example 2

The following compound was synthesized by the same process as that in Example 1:

Ethyl 8-(4-aminophenyl)-1-cyclopropyl-9-methyl-4-oxo-4H-quinolizine-3-carboxylate $^1$H-NMR(CDCl$_3$) δ: 0.74–0.78(2H, m), 1.00–1.04(2H, m), 1.43(3H, t, J=7.3 Hz), 2.32–2.39(1H, m), 2.85(3H, s), 3.92(2H, brs), 4.43(2H, q, J=7.3 Hz), 6.77–6.80(2H, m), 7.12(1H, d, J=7.3 Hz), 7.22–7.26(2H, m), 8.38(1H, s), 9.43(1H, d, J=7.3 Hz)

Example 3

Ethyl 8-(4-acetylphenyl)-1-cyclopropyl-9-methyl-4-oxo-4H-quinolizine-3-carboxylate $^1$H-NMR(CDCl$_3$) δ: 0.78–1.07(4H, m), 1.44(3H, t, J=7.1 Hz), 2.33–2.40(1H, m), 2.68(3H, s), 2.82(3H, s), 4.44(2H, q, J=7.1 Hz), 7.06(1H, d, J=7.6 Hz), 7.51(2H, d, J=8.5 Hz), 8.10(2H, d, J=8.5 Hz), 8.44(1H, s), 9.48(1H, d, J=7.6 Hz)

Example 4

Ethyl 8-(3-acetylphenyl)-1-cyclopropyl-9-methyl-4-oxo-4H-quinolizine-3-carboxylate $^1$H-NMR(CDCl$_3$) δ: 0.79–1.07(4H, m), 1.44(3H, t, J=7.0 Hz), 2.33–2.40(1H, m), 2.67(3H, s), 2.81(3H, s), 4.44(2H, q, J=7.0 Hz), 7.07–8.06(5H, m), 8.43(1H, s), 9.49(1H, d, J=7.4 Hz)

Example 5

Ethyl 1-cyclopropyl-8-(4-formylphenyl)-9-methyl-4-oxo-4H-quinolizine-3-carboxylate $^1$H-NMR(CDCl$_3$) δ: 0.79–0.83(2H, m), 1.03–1.08(2H, m), 1.44(3H, t, J=7.3 Hz), 2.33–2.40(1H, m), 2.82(3H, s), 4.44(2H, q, J=7.3 Hz), 7.06(1H, d, J=7.3 Hz), 7.58(2H, d, J=8.3 Hz), 8.04(2H, d, J=8.3 Hz), 8.45(1H, s), 9.49(1H, d, J=7.3 Hz), 10.12(1H, s)

Example 6

Ethyl 1-cyclopropyl-9-methyl-4-oxo-8-p-tolyl-4H-quinolizine-3-carboxylate $^1$H-NMR(CDCl$_3$) δ: 0.76–1.05(4H, m), 1.44(3H, t, J=7.1 Hz), 2.33–2.39(1H, m), 2.45(3H, s), 2.83(3H, s), 4.43(2H, q, J=7.1 Hz), 7.10(1H, d, J=7.6 Hz), 7.26–7.33(4H, m), 8.41 (1H, s), 9.46(1H, d, J=7.6 Hz)

Example 7

Ethyl 1-cyclopropyl-8-(6-methoxypyridin-3-yl)-9-methyl-4-oxo-4H-quinolizine-3-carboxylate $^1$H-NMR(CDCl$_3$) δ: 0.77–0.79(2H, m), 1.02–1.05(2H, m), 1.44(3H, t, J=7.1 Hz), 2.36(1H, m), 2.85(3H, s), 4.02 (3H, s), 4.44(2H, q, J=7.1 Hz), 6.90(1H, d, J=8.1 Hz), 7.06(1H, d, J=7.3 Hz), 7.63–7.68(1H, m), 8.25(1H, d, J=2.4 Hz), 8.43(1H, s), 9.46(1H, d, J=7.3 Hz)

Example 8

Ethyl 1-cyclopropyl-9-methyl-4-oxo-8-(pyridin-3-yl)-4H-quinolizine-3-carboxylate $^1$H-NMR(CDCl$_3$) δ: 0.78–0.83(2H, m), 1.04–1.09(2H, m), 1.44(3H, t, J=7.1 Hz), 2.36(1H, m), 2.85(3H, s), 4.43 (2H, q, J=7.1 Hz), 7.07(1H, d, J=7.3 Hz), 7.48–7.51(1H, m), 7.77–7.80(1H, m), 8.44(1H, s), 8.69–8.74(2H, m), 9.47(1H, d, J=7.3 Hz)

Example 9

Ethyl 1-cyclopropyl-9-methyl-4-oxo-8-o-tolyl-4H-quinolizine-3-carboxylate $^1$H-NMR(CDCl$_3$) δ: 0.73–0.80(2H, m), 0.98–1.06(2H, m), 1.44(3H, t, J=7.1 Hz), 2.14(3H, s), 2.34–2.38(1H, m), 2.69(3H, s), 4.44(2H, q, J=7.1 Hz), 6.99(1H, d, J=7.3 Hz), 7.13(1H, d, J=7.3 Hz), 7.29–7.37(3H, m), 8.42(1H, s), 9.48(1H, d, J=7.3 Hz)

Example 10

Ethyl 1-cyclopropyl-8-(2-formylphenyl)-9-methyl-4-oxo-4H-quinolizine-3-carboxylate $^1$H-NMR(CDCl$_3$) δ: 0.79–0.82(2H, m), 0.99–1.04(2H, m), 1.44(3H, t, J=7.1 Hz), 2.31–2.35(1H, m), 2.68(3H, s), 4.44(2H, q, J=7.1 Hz), 7.00(1H, d, J=7.3 Hz), 7.34(1H, d, J=7.7 Hz), 7.63–7.78(2H, m), 8.07(1H, d, J=7.7 Hz), 8.45 (1H, s), 9.49(1H, d, J=7.3 Hz), 9.93(1H, s)

Example 11

Ethyl 8-(4-cyanophenyl)-1-cyclopropyl-9-methyl-4-oxo-4H-quinolizine-3-carboxylate $^1$H-NMR(CDCl$_3$) δ: 0.78–0.82(2H, m), 1.03–1.08(2H, m), 1.44(3H, t, J=7.1 Hz), 2.34–2.37(1H, m), 2.80(3H, s), 4.44(2H, q, J=7.1 Hz), 7.01(1H, d, J=7.4 Hz), 7.52(2H, d, J=8.1 Hz), 7.82(2H, d, J=8.1 Hz), 8.45(1H, s), 9.48(1H, d, J=7.4 Hz)

Example 12

Ethyl 8-(4-tert-butoxycarbonylamino-3,5-dimethylphenyl)-1-cyclopropyl-9-methyl-4-oxo-4H-quinolizine-3-carboxylate $^1$H-NMR(CDCl$_3$) δ: 0.77–0.81(2H, m), 1.01–1.06(2H, m), 1.35(3H, t, J=7.1 Hz), 1.74–1.81(1H, m), 2.36(9H, s), 2.82(3H, s), 2.88(3H, s), 2.96(3H, s), 4.43(2H, q, J=7.1 Hz), 7.01–7.08(3H, m), 8.02(1H, s), 8.40(1H, s), 9.458(1H, d, J=7.3 Hz)

Example 13

Ethyl 1-cyclopropyl-9-methyl-8-(3-nitrophenyl)-4-oxo-4H-quinolizine-3-carboxylate $^1$H-NMR(CDCl$_3$) δ: 0.80–1.13(4H, m), 1.44(3H, t, J=7.11 Hz), 2.34–2.41(1H, m), 2.84(3H, s), 4.44(2H, q, J=7.1 Hz), 7.06(1H, d, J=7.6 Hz), 7.70–7.78(2H, m), 8.29–8.45(2H, m), 8.65(1H, s), 9.48(1H, d, J=7.6 Hz)

Example 14

39 mg of ethyl 1-cyclopropyl-9-methyl-8-(3-nitrophenyl)-4-oxo-4H-quinolizine-3-carboxylate (Example 13) was dissolved in 2 ml of ethanol. 5 mg of 5% palladium carbon was added to the obtained solution, and they were stirred at room temperature in hydrogen atmosphere for 14 hours. The catalyst was taken by the filtration. Water was added to the filtrate. After the extraction with chloroform, the organic layer was dried over anhydrous magnesium sulfate. The solvent was evaporated under reduced pressure, and the residue was purified by the silica gel column chromatography (eluent: chloroform/methanol=100/1) to obtain 22 mg of ethyl 1-cyclopropyl-8-(3-ethylaminophenyl)-9-methyl-4-oxo-4H-quinolizine-3-carboxylate.

$^1$H-NMR(CDCl$_3$) δ: 0.76–1.45(10H, m), 2.28–2.41(1H, m), 2.84(3H, s), 3.21(2H, q, J=7.1 Hz), 4.43(2H, q, J=7.1 Hz), 6.55–7.30(5H, m), 8.40(1H, s), 9.45–9.47(1H, m)

Example 15

50 mg of ethyl 8-(4-acetylphenyl)-1-cyclopropyl-9-methyl-4-oxo-4H-quinolizine-3-carboxylate (Example 3) was dissolved in 1 ml of ethanol. 9 mg of sodium borohydride was added to the obtained solution, and they were stirred at room temperature for 14 hours. Water was added to the reaction mixture. After the extraction with chloroform, the organic layer was dried over anhydrous sodium sulfate. The solvent was evaporated under reduced pressure, and the obtained residue was purified by the silica gel column chromatography (eluent: chloroform/methanol=100/3) to obtain 35 mg of ethyl 1-cyclopropyl-8-[4-(1-hydroxyethyl)phenyl]-9-methyl-4-oxo-4H-quinolizine-3-carboxylate.

$^1$H-NMR(CDCl$_3$) δ: 0.76–1.06(4H, m), 1.44(3H, t, J=7.1 Hz), 1.57(3H, d, J=6.6 Hz), 2.33–2.40(1H, m), 2.83(3H, s), 4.23(2H, q, J=7.1 Hz), 5.01(1H, q, J=6.6 Hz), 7.06(1H, d, J=7.6 Hz), 7.36(2H, d, J=8.3 Hz), 7.53(2H, d, J=8.3 Hz), 8.41(1H, s), 9.41(1H, d, J=7.6 Hz)

Example 16

The following compound was synthesized by the same process as that in Example 15:

Ethyl 1-cyclopropyl-8-[3-(1-hydroxyethyl)phenyl]-9-methyl-4-oxo-4H-quinolizine-3-carboxylate $^1$H-NMR(CDCl$_3$) δ: 0.76–1.06(4H, m), 1.43(3H, t, J=7.3 Hz), 1.56(3H, d, J=6.6 Hz), 2.32–2.38(1H, m), 2.82(3H, s), 4.42(2H, q, J=7.3 Hz), 5.01(1H, q, J=6.6 Hz), 7.07(1H, d, J=7.3 Hz), 7.26–7.48(4H, m), 8.39(1H, s), 9.43(1H, d, J=7.3 Hz)

Example 17

50 mg of ethyl 8-(4-acetylphenyl)-1-cyclopropyl-9-methyl-4-oxo-4H-quinolizine-3-carboxylate (Example 3) was dissolved in 2 ml of ethanol. 13 mg of hydroxylamine hydrochloride was added to the obtained solution, and they were stirred under reflux for 6 hours. Water was added to the reaction mixture. After the extraction with chloroform, the organic layer was dried over anhydrous sodium sulfate. The solvent was evaporated under reduce pressure, and the obtained residue was purified by the silica gel column chromatography (eluent: chloroform/methanol=50/1) to obtain 47 mg of ethyl 1-cyclopropyl-8-[4-(1-hydroxyiminoethyl)phenyl]-9-methyl-4-oxo-4H-quinolizine-3-carboxylate.

$^1$H-NMR(CDCl$_3$) δ: 0.77–1.07(4H, m), 1.44(3H, t, J=7.4 Hz), 2.29–2.39(4H, m), 2.84(3H, s), 4.45(2H, q, J=7.4 Hz), 7.10(1H, d, J=7.6 Hz), 7.41–7.43(2H, m), 7.77–7.80(2H, m), 8.43(1H, s), 9.51(1H, d, J=7.6 Hz)

Example 18

The following compound was synthesized by the same process as that in Example 17:

Ethyl 1-cyclopropyl-8-[3-(1-hydroxyiminoethyl)phenyl]-9-methyl-4-oxo-4H-quinolizine-3-carboxylate $^1$H-NMR(CDCl$_3$) δ: 0.77–1.06(4H, m), 1.44(3H, t, J=7.1 Hz), 2.28–2.39(4H, m), 2.82(3H, s), 4.44(2H, q, J=7.1 Hz), 7.10(1H, d, J=7.1 Hz), 7.37–7.71(4H, m), 8.42(1H, s), 9.49(1H, d, J=7.1 Hz)

Example 19

Ethyl 1-cyclopropyl-8-[4-(1-methoxyiminoethyl)phenyl]-9-methyl-4-oxo-4H-quinolizine-3-carboxylate $^1$H-NMR(CDCl$_3$) δ: 0.77–1.07(4H, m), 1.44(3H, t, J=7.1 Hz), 2.29(3H, s), 2.33–2.40(1H, m), 2.83(3H, s), 4.04(3H, s), 4.43(2H, q, J=7.1 Hz), 7.10(1H, d, J=7.6 Hz), 7.42(2H, d, J=8.3 Hz), 7.80(2H, d, J=8.3 Hz), 8.41(1H, s), 9.46(1H, d, J=7.6 Hz)

Example 20

50 mg of ethyl 8-(4-aminophenyl)-1-cyclopropyl-9-methyl-4-oxo-4H-quinolizine-3-carboxylate (Example 2) was dissolved in 2 ml of DMF. 20 mg of methyl iodide and 29 mg of potassium carbonate were added to the obtained solution, and they were stirred at 70° C. for 17 hours. Water was added to the reaction mixture. After the extraction with chloroform, the organic layer was dried over anhydrous sodium sulfate. The solvent was evaporated under reduced pressure, and the obtained residue was purified by the silica gel column chromatography (eluent: chloroform/ethyl acetate=9/1) to obtain 16 mg of ethyl 1-cyclopropyl-9-methyl-8-(4-methylaminophenyl)-4-oxo-4H-quinolizine-3-carboxylate.

$^1$H-NMR(CDCl$_3$) δ: 0.74–0.78(2H, m), 1.00–1.04(2H, m), 1.43(3H, t, J=7.1 Hz), 2.31–2.40(1H, m), 2.86(3H, s), 2.92(3H, s), 4.43(2H, q, J=7.1 Hz), 6.69–6.73(2H, m), 7.14(1H, d, J=7.1 Hz), 7.26–7.29(2H, m), 8.37(1H, s), 9.43(1H, d, J=7.1 Hz)

Example 21

The following compound was synthesized by the same process as that in Example 20:

Ethyl 1-cyclopropyl-9-methyl-4-oxo-8-{4-[2-(tetrahydropyran-2-yloxy)-ethylamino]phenyl}-4H-quinolizine-3-carboxylate $^1$H-NMR(CDCl$_3$) δ: 0.75–0.78(2H, m), 1.00–1.03(2H, m), 1.43(3H, t, J=7.3 Hz), 1.53–1.88(6H, m), 2.32–2.39(1H, m), 2.86(3H, s), 3.36–4.01(6H, m), 4.42(2H, q, J=7.3 Hz), 4.63–4.65(1H, m), 6.73–6.75(2H, m), 7.14(1H, d, J=7.3 Hz), 7.25–7.29(2H, m), 8.38(1H, s), 9.43(1H, d, J=7.3 Hz)

Example 22

50 mg of ethyl 8-(4-aminophenyl)-1-cyclopropyl-9-methyl-4-oxo-4H-quinolizine-3-carboxylate (Example 2) was dissolved in 2 ml of pyridine. 17 mg of acetic anhydride was added to the obtained solution, and they were stirred at room temperature for 16 hours. Water was added to the reaction mixture. After the extraction with chloroform, the organic layer was dried over anhydrous sodium sulfate. The solvent was evaporated under reduce pressure, and the obtained residue was purified by the silica gel column chromatography (eluent: chloroform/ethyl acetate=4/1) to obtain 55 mg of ethyl 8-(4-acetylaminophenyl)-1-cyclopropyl-9-methyl-4-oxo-4H-quinolizine-3-carboxylate.

$^1$H-NMR(CDCl$_3$) δ: 0.74–0.78(2H, m), 1.01–1.06(2H, m), 1.41(3H, t, J=7.1 Hz), 2.24(3H, s), 2.30–2.39(1H, m), 2.83(3H, s), 4.40(2H, q, J=7.1 Hz), 7.09(1H, d, J=7.1 Hz), 7.33(2H, d, J=8.6 Hz), 7.78(2H, d, J=8.6 Hz), 8.40(1H, s), 9.42(1H, d, J=7.1 Hz)

Example 23

100 mg of ethyl 8-(4-aminophenyl)-1-cyclopropyl-9-methyl-4-oxo-4H-quinolizine-3-carboxylate (Example 2) was dissolved in 1.5 ml of THF. 1.5 ml of 2 N sodium hydrogenphosphonate and 1.5 ml of 36% formalin were added to the obtained solution, and they were stirred at 60° C. for 17 hours. After the extraction with chloroform, the organic layer was dried over anhydrous sodium sulfate. The solvent was evaporated under reduce pressure, and the obtained residue was purified by the silica gel column chromatography (eluent: chloroform/ethyl acetate=9/1) to obtain 69 mg of ethyl 1-cyclopropyl-8-(4-dimethylaminophenyl)-9-methyl-4-oxo-4H-quinolizine-3-carboxylate.

$^1$H-NMR(CDCl$_3$) δ: 0.66–0.70(2H, m), 0.92–0.97(2H, m), 1.36(3H, t, J=7.1 Hz), 2.25–2.31(1H, m), 2.79(3H, s), 2.97(6H, s), 4.35(2H, q, J=7.1 Hz), 6.72(2H, d, J=8.8 Hz), 7.07(1H, d, J=7.6 Hz), 7.25(2H, d, J=8.8 Hz), 8.29(1H, s), 9.36(1H, d, J=7.6 Hz)

Example 24

350 mg of ethyl 8-chloro-1-cyclopropyl-9-methyl-4-oxo-4H-quinolizine-3-carboxylate was dissolved in 3.5 ml of toluene. 1.8 ml of ethanol, 1.8 ml of 2 M aqueous sodium carbonate solution, 235 mg of 4-aminomethylphenylboronic acid hydrochloride and 40 mg of bis(triphenylphosphine)palladium (II) chloride were added to the obtained solution, and they were heated under reflux in argon atmosphere for 6 hours. The reaction mixture was acidified with 1 N hydrochloric acid. After washing the aqueous layer with ethyl acetate, it was taken and then concentrated under reduced pressure. 2 ml of methanol and 1 ml of 1 N sodium hydroxide were added to the obtained residue, and they were stirred at 50° C. for 1 hour. The reaction mixture was concentrated under reduced pressure, and the residue was dissolved in 10 ml of water and then neutralized with 1 N hydrochloric acid. The crystals thus formed were taken by the filtration to obtain 241 mg of 8-(4-aminomethylphenyl)-1-cyclopropyl-9-methyl-4-oxo-4H-quinolizine-3-carboxylic acid.

$^1$H-NMR(CF$_3$COOD) δ: 1.14–1.16(2H—, m), 1.50–1.52 (2H, m), 2.79(1H, m), 3.24(3H, s), 4.66(2H, s), 7.46(1H, bs), 7.74(2H, d, J=7.5 Hz), 7.87(2H, d, J=7.5 Hz), 8.01(1H, d, J=7.3 Hz), 8.84(1H, s), 9.56(1H, d, J=7.3 Hz) FAB-MS m/z: 349(M+H)$^+$

Example 25

100 mg of ethyl 8-chloro-1-cyclopropyl-9-methoxy-4-oxo-4H-quinolizine-3-carboxylate was suspended in 1 ml of toluene. 0.5 ml of ethanol, 0.25 ml of 2 M aqueous sodium carbonate solution, 61 mg of 2-(N,N-dimethylaminomethyl)phenylboronic acid and 10 mg of bis(triphenylphosphine) palladium (II) chloride were added to the obtained solution, and they were heated under reflux in argon atmosphere for 38 hours. Ethyl acetate was added to the reaction mixture. The organic layer was taken, washed with water and dried over anhydrous sodium sulfate. The solvent was evaporated under reduced pressure. The resultant residue was purified by the silica gel column chromatography (eluent: chloroform/acetone=4/1) to obtain 59 mg of 1-cyclopropyl-8-(2-dimethylaminomethylphenyl)-9-methoxy-4-oxo-4H-quinolizine-3-carboxylic acid.

$^1$H-NMR(CDCl$_3$) δ: 0.70–0.90(2H, m), 0.99–1.01(2H, m), 2.10(6H, s), 2.56–2.64(1H, m), 3.40(2H, bs), 3.43(3H, s), 7.35–7.63(5H, m), 8.44(1H, s), 9.27(1H, d, J=7.3 Hz) FAB-MS m/z: 393(M+H)$^+$

Example 26

2 ml of methanol and 0.5 ml of 1 N sodium hydroxide were added to 51 mg of ethyl 8-(3-aminophenyl)-1-cyclopropyl-9-methyl-4-oxo-4H-quinolizine-3-carboxylate, and they were stirred at 50° C. for 2 hours. The reaction mixture was concentrated under reduced pressure and then dissolved in 10 ml of water. The obtained solution was neutralized with 1 N hydrochloric acid. The crystals thus formed were taken by the filtration to obtain 36 mg of 8-(3-aminophenyl)-1-cyclopropyl-9-methyl-4-oxo-4H-quinolizine-3-carboxylic acid.

$^1$H-NMR(CDCl$_3$) δ: 0.82–0.86(2H, m), 1.07–1.11(2H, m), 2.40(1H, m), 2.90(3H, s), 3.86(2H, brs), 6.66–7.32(5H, m), 8.58(1H, s), 9.37(1H, d, J=7.3 Hz), 14.10(1H, hrs) FAB-MS m/z: 335(M+H)$^+$

Example 27

The following compound was synthesized by the same process as that in Example 26:

8-(4-Aminophenyl)-1-cyclopropyl-9-methyl-4-oxo-4H-quinolizine-3-carboxylic acid $^1$H-NMR(CDCl$_3$) δ: 0.80–0.84(2H, m), 1.06–1.12(2H, m), 2.37–2.44(1H, m), 2.91(3H, s), 3.97(2H, brs), 6.79–6.82 (2H, m), 7.23–7.31(3H, m), 8.54(1H, s), 9.34(1H, d, J=7.4 Hz) FAB-MS m/z: 335(M+H)$^+$

Example 28

8-(4-Acetylphenyl)-1-cyclopropyl-9-methyl-4-oxo-4H-quinolizine-3-carboxylic acid $^1$H-NMR(CDCl$_3$) δ: 0.85–0.89(2H, m), 1.09–1.14(2H, m), 2.39–2.45(1H, m), 2.69(3H, s), 2.89(3H, s), 7.25(1H, d, J=7.3 Hz), 7.52(2H, dd, J=6.6, 2.2 Hz), 8.13(2H, dd, J=6.6, 2.2 Hz), 8.62(1H, s), 9.40(1H, d, J=7.3 Hz), 14.02(1H, brs) FAB-MS m/z: 362(M+H)$^+$

Example 29

8-(3-Acetylphenyl)-1-cyclopropyl-9-methyl-4-oxo-4H-quinolizine-3-carboxylic acid $^1$H-NMR(CDCl$_3$) δ: 0.85–0.90(2H, m), 1.09–1.14(2H, m), 2.40–2.45(1H, m), 2.69(3H, s), 2.88(3H, s), 7.28–8.09 (5H; m), 8.62(1H, s), 9.41(1H, d, J=7.3 Hz), 14.03(1H, brs) FAB-MS m/z: 362(M+H)$^+$

Example 30

1-Cyclopropyl-8-(4-formylphenyl)-9-methyl-4-oxo-4H-quinolizine-3-carboxylic acid $^1$H-NMR(CDCl$_3$) δ: 0.83–0.87(2H, m), 1.08–1.12(2H, m), 2.37–2.43(1H, m), 2.87(3H, s), 7.23(1H, d, J=7.3 Hz), 7.56–7.59(2H, m), 8.03–8.06(2H, m), 8.60(1H, d, J=0.7 Hz), 9.38(1H, d, J=0.7, 7.3 Hz), 10.11(1H, s) FAB-MS m/z: 348(M+H)$^+$

Example 31

1-Cyclopropyl-9-methyl-4-oxo-8-p-tolyl-4H-quinolizine-3-carboxylic acid $^1$H-NMR(CF$_3$COOD) δ: 1.18–1.22(2H, m), 1.54–1.59 (2H, m), 2.66(3H, s), 2.82–2.89(1H, m), 3.34(3H, s), 7.59–7.64(4H, m), 8.14(1H, d, J=7.3 Hz), 8.84(1H, s), 9.58(1H, d, J=7.3 Hz) FAB-MS m/z: 334(M+H)$^+$

Example 32

1-Cyclopropyl-8-(6-methoxypyridin-3-yl)-9-methyl-4-oxo-4H-quinolizine-3-carboxylic acid $^1$H-NMR(CD$_3$OD) δ: 0.82–0.86(2H, m), 1.11–1.16(2H, m), 2.51–2.53(1H, m), 2.95(3H, s), 4.01(3H, s), 6.90(1H, dd, J=0.73, 8.8 Hz), 7.49(1H, d, J=7.3 Hz), 7.88(1H, dd, J=0.73, 8.8 Hz), 8.34(1H, t, J=0.73 Hz), 8.44(1H, s), 9.42(1H, d, J=7.3 Hz) FAB-MS m/z: 351(M+H)$^+$

Example 33

1-Cyclopropyl-9-methyl-4-oxo-8-(pyridin-3-yl)-4H-quinolizine-3-carboxylic acid $^1$H-NMR(CD$_3$OD) δ: 0.85–0.89(2H, m), 1.10–1.15(2H, m), 2.40–2.44(1H, m), 2.91(3H, s), 7.26(1H, d, J=7.5 Hz), 7.51(1H, dd, J=4.9, 7.8 Hz), 7.78(1H, m), 8.60(1H, s), 8.71(1H, d, J=2.2 Hz), 8.76(1H, dd, J=1.5, 4.9 Hz), 9.40(1H, d, J=7.5 Hz), 13.97(1H, brs) FAB-MS m/z: 321(M+H)$^+$

Example 34

1-Cyclopropyl-9-methyl-4-oxo-8-o-tolyl-4H-quinolizine-3-carboxylic acid $^1$H-NMR(CDCl$_3$) δ: 0.84–0.86(2H, m), 1.07–1.09(2H, m), 2.38–2.45(1H, m), 2.76(3H, s), 7.13(1H, d, J=7.4 Hz), 7.18(1H, d, J=7.3 Hz), 7.32–7.40(3H, m), 8.61(1H, s), 9.40(1H, d, J=7.4 Hz) FAB-MS m/z: 334(M+H)$^+$

Example 35

1-Cyclopropyl-8-(2-formylphenyl)-9-methyl-4-oxo-4H-quinolizine-3-carboxylic acid $^1$H-NMR(CDCl$_3$) δ: 0.85–0.88(2H, m), 1.05–1.09(2H, m), 2.35–2.42(1H, m), 2.73(3H, s), 7.17(1H, d, J=7.4 Hz), 7.34(1H, d, J=7.6 Hz), 7.69–7.73(1H, m), 7.77–7.81(1H, m), 8.07(1H, d, J=7.6 Hz), 8.62(1H, s), 9.40(1H, d, J=7.4 Hz), 9.99(1H, s) FAB-MS m/z: 348(M+H)$^+$

Example 36

8-(4-Cyanophenyl)-1-cyclopropyl-9-methyl-4-oxo-4H-quinolizine-3-carboxylic acid $^1$H-NMR(CDCl$_3$) δ: 0.86–0.87(2H, m), 1.11–1.13(2H, m), 2.39–2.43(1H, m), 2.87(3H, s), 7.20(1H, d, J=7.3 Hz), 7.54(2H, d, J=8.0 Hz), 7.86(2H, d, J=8.0 Hz), 8.64(1H, s), 9.40(1H, d, J=7.3 Hz) FAB-MS m/z: 345(M+H)$^+$

Example 37

1-Cyclopropyl-8-(3-ethylaminophenyl)-9-methyl-4-oxo-4H-quinolizine-3-carboxylic acid $^1$H-NMR(CDCl$_3$) δ: 0.83–1.32(7H, m), 2.37–2.45(1H, m), 2.90(3H, s), 3.21(2H, q, J=7.1 Hz), 6.54–6.72(3H, m), 7.29–7.33(2H, m), 8.57(1H, s), 9.37(1H, d, J=7.1 Hz) FAB-MS m/z: 363(M+H)$^+$

Example 38

1-Cyclopropyl-8-[4-(1-hydroxyiminoethyl)phenyl]-9-methyl-4-oxo-4H-quinolizine-3-carboxylic acid $^1$H-NMR(CDCl$_3$) δ: 0.84–0.88(2H, m), 1.08–1.13(2H, m), 2.35(3H, s), 2.37–2.42(1H, m), 2.90(3H, s), 7.28(1H, d, J=7.3 Hz), 7.43(2H, dd, J=1.7, 6.6 Hz), 7.82(2H, dd, J=1.7, 6.6 Hz), 8.61(1H, s), 9.39(1H, d, J=7.3 Hz), 14.06(1H, brs) FAB-MS m/z: 377(M+H)$^+$

Example 39

1-Cyclopropyl-8-[3-(1-hydroxyiminoethyl)phenyl]-9-methyl-4-oxo-4H-quinolizine-3-carboxylic acid $^1$H-NMR(CDCl$_3$) δ: 0.85–0.89(2H, m), 1.08–1.13(2H, m), 2.34(3H, s), 2.36–2.42(1H, m), 2.90(3H, s), 7.26–7.45(5H, m), 8.61(1H, s), 9.40(1H, d, J=7.3 Hz), 14.07(1H, brs) FAB-MS m/z: 377(M+H)$^+$

Example 40

1-Cyclopropyl-8-[4-(1-methoxyiminoethyl)phenyl]-9-methyl-4-oxo-4H-quinolizine-3-carboxylic acid $^1$H-NMR(CF$_3$COOD) δ: 1.08–1.48(4H, m), 2.68–2.75(1H, m), 3.01(3H, s), 3.17(3H, s), 4.48(3H, s), 7.85(2H, d, J=8.1 Hz), 7.93(1H, d, J=7.3 Hz), 8.10(2H, d, J=8.1 Hz), 8.80(1H, s), 9.52(1H, d, J=7.3 Hz) FAB-MS m/z: 391(M+H)$^+$

Example 41

1-Cyclopropyl-9-methyl-8-(4-methylaminophenyl)-4-oxo-4H-quinolizine-3-carboxylic acid $^1$H-NMR(CDCl$_3$) δ: 0.80–0.84(2H, m), 1.06–1.11(2H, m), 2.38–2.44(1H, m), 2.93(6H, s), 6.73(2H, d, J=8.5 Hz), 7.29–7.33(3H, m), 8.54(1H, s), 9.34(1H, d, J=7.6 Hz) FAB-MS m/z: 349(M+H)$^+$

Example 42

8-(4-Acetylaminophenyl)-1-cyclopropyl-9-methyl-4-oxo-4H-quinolizine-3-carboxylic acid $^1$H-NMR(CDCl$_3$) δ: 0.84–0.88(2H, m), 1.11–1.16(2H, m), 2.21(3H, s), 2.43–2.49(1H, m), 2.94(3H, s), 7.38–7.44(3H, m), 7.77(2H, d, J=8.6 Hz), 8.51(1H, s), 9.38(1H, d, J=7.3 Hz)

Example 43

1-Cyclopropyl-8-(4-dimethylaminophenyl)-9-methyl-4-oxo-4H-quinolizine-3-carboxylic acid $^1$H-NMR(CDCl$_3$) δ: 0.80–0.84(2H, m), 1.06–1.11(2H, m), 2.38–2.45(1H, m), 2.94(3H, s), 3.07(6H, s), 6.82(2H, d, J=8.8 Hz), 7.32–7.36(3H, m), 8.53(1H, s), 9.33(1H, d, J=7.6 Hz) FAB-MS m/z: 363(M+H)$^+$

Example 44

1-Cyclopropyl-8-[4-(1-hydroxyethyl)phenyl]-9-methyl-4-oxo-4H-quinolizine-3-carboxylic acid $^1$H-NMR(CDCl$_3$) δ: 0.84–0.88(2H, m), 1.08–1.13(2H, m), 1.58(3H, d, J=6.6 Hz), 2.38–2.45(1H, m), 2.90(3H, s), 5.00–5.05(1H, m), 7.28(1H, d, J=7.3 Hz), 7.40(2H, dd, J=1.9, 6.3 Hz), 7.56(2H, dd, J=1.9, 6.3 Hz), 8.60(1H, s), 9.38(1H, d, J=7.3 Hz), 14.08(1H, brs) FAB-MS m/z: 364(M+H)$^+$

Example 45

1-Cyclopropyl-8-[3-(1-hydroxyethyl)phenyl]-9-methyl-4-oxo-4H-quinolizine-3-carboxylic acid $^1$H-NMR(CDCl$_3$) δ: 0.84–1.13(4H, m), 1.53–1.58(3H, m), 2.40–2.47(1H, m), 2.90(3H, s), 5.00–5.05(1H, m), 7.22–7.53(5H, m), 8.60(1H, s), 9.39(1H, d, J=7.3 Hz), 14.08(1H, brs) FAB-MS m/z: 364(M+H)$^+$

Example 46

12 mg of ethyl 1-cyclopropyl-9-methyl-4-oxo-8-{4-[2-(tetrahydro-pyran-2-yloxy)-ethylamino]phenyl}-4H-quinolizine-3-carboxylate (Example 21) was dissolved in 1 ml of ethanol. 1 ml of water and 10 mg of pyridinium p-toluenesulfonate were added to the obtained solution, and they were stirred at 50° C. for 9 hours. The reaction mixture was poured into an aqueous sodium hydrogencarbonate solution. After extracting with chloroform, the organic layer was dried over anhydrous sodium sulfate. The solvent was evaporated under reduced pressure. The obtained residue was purified by the silica gel column chromatography (eluent: chloroform/methanol=19/1). 1 ml of ethanol and 1 ml of 1 N sodium hydroxide were added to the obtained crystals, and they were stirred at 50° C. for 2 hours. The reaction mixture was concentrated under reduced pressure and then dissolved in 5 ml of water. The obtained solution was neutralized with 1 N hydrochloric acid. The crystals thus formed were taken by the filtration to obtain 1 mg of 1-cyclopropyl-8-[4-(2-hydroxyethylamino)phenyl]-9-methyl-4-oxo-4H-quinolizine-3-carboxylic acid.

$^1$H-NMR(CDCl$_3$) δ: 0.81–0.85(2H, m), 1.10–1.15(2H, m), 2.42–2.48(1H, m), 2.96(3H, s), 3.33–3.36(2H, m), 3.82–3.85(2H, m), 6.79(2H, d, J=8.8 Hz), 7.31–7.43(3H, m), 8.46(1H, s), 9.34(1H, d, J=7.6 Hz) FAB-MS m/z: 379(M+H)$^+$

Example 47

14 mg of ethyl 8-(4-tert-butoxycarbonylamino-3,5-dimethylphenyl)-1-cyclopropyl-9-methyl-4-oxo-4H-quinolizine-3-carboxylate (Example 12) was dissolved in 1 ml of THF. 1 ml of 3 N hydrochloric acid was added to the obtained solution, and they were stirred at 50° C. for 3 hours.

2 ml of 3 N sodium hydroxide was added to the reaction mixture, and they were stirred at 50° C. for 14 hours and then neutralized with 1 N hydrochloric acid. The crystals thus precipitated were taken by the filtration to obtain 4 mg of 8-(4-amino-3,5-dimethylphenyl)-1-cyclopropyl-9-methyl-4-oxo-4H-quinolizine-3-carboxylic acid.

$^1$H-NMR(CDCl$_3$) δ: 0.82–0.86(2H, m), 1.07–1.12(2H, m), 2.27(6H, s), 2.37–2.43(1H, m), 2.92(3H, s), 7.03(2H, s), 7.31(1H, d, J=7.4 Hz), 8.54(1H, s), 9.34(1H, d, J=7.4 Hz) FAB-MS m/z: 362(M+H)$^+$

Example 48

The following compound was synthesized by the same process as that in Example 1:

Ethyl 1-cyclopropyl-8-(5-formylthiophen-2-yl)-9-methyl-4-oxo-4H-quinolizine-3-carboxylate $^1$H-NMR(CDCl$_3$) δ: 0.76–0.82(2H, m), 102–1.09(2H, m), 1.53(3H, t, J=7.1 Hz), 2.32–2.39(1H, m), 2.98(3H, s), 4.44(2H, q, J=7.1 Hz), 7.13(1H, d, J=7.3 Hz), 7.37(1H, d, J=3.7 Hz), 7.84(1H, d, J=3.7 Hz), 8.44(1H, s), 9.40(1H, d, J=7.3 Hz), 9.99(1H, s)

Example 49

Ethyl 8-(3-amino-4-methylphenyl)-1-cyclopropyl-9-methyl-4-oxo-4H-quinolizine-3-carboxylate $^1$H-NMR(CDCl$_3$) δ: 0.75–0.79(2H, m), 0.99–1.04(2H, m), 1.43(3H, t, J=7.1 Hz), 2.24(3H, s), 2.32–2.38(1H, m), 2.83(3H, s), 3.84(2H, brs), 4.42(2H, q, J=7.1 Hz), 6.69–6.71(2H, m), 7.08–7.17(2H, m), 8.39(1H, s), 9.43(1H, d, J=7.6 Hz)

Example 50

Ethyl 8-[4-(2-amino-2-carboxyethyl)phenyl]-1-cyclopropyl-9-methyl-4-oxo-4H-quinolizine-3-carboxylate $^1$H-NMR(DMSO-d$_6$) δ: 0.70–0.73(2H, m), 0.99–1.04(2H, m), 1.30(3H, t, J=7.1 Hz), 2.41–2.50(1H, m), 2.81(3H, s), 2.92–3.49(3H, m), 4.26(2H, q, J=7.11 Hz), 7.27–7.30(1H, m), 7.42–7.48(4H, m), 8.18(1H, s), 9.29(1H, d, J=7.4 Hz)

Example 51

Ethyl 1-cyclopropyl-8-(4-hydroxymethylphenyl)-9-methyl-4-oxo-4H-quinolizine-3-carboxylate $^1$H-NMR(CDCl$_3$) δ: 0.76–0.79(2H, m), 1.01–1.05(2H, m), 1.41–1.45(3H, m), 2.34–2.38(1H, m), 2.82(3H, s), 4.40–4.45(2H, m), 4.81(2H, s), 7.06(1H, d, J=7.6 Hz), 7.35–7.38(2H, m), 7.51–7.53(2H, m), 8.40(1H, s), 9.40(1H, d, J=7.6 Hz)

Example 52

Ethyl 8-(3-cyanophenyl)-1-cyclopropyl-9-methyl-4-oxo-4H-quinolizine-3-carboxylate $^1$H-NMR(CDCl$_3$) δ: 0.79–0.83(2H, m), 1.06–1.11(2H, m), 1.44(3H, t, J=7.1 Hz), 2.35–2.41(1H, m), 2.82(3H, s), 4.44(2H, q, J=7.1 Hz), 7.06(1H, d, J=7.3 Hz), 7.64–7.72(3H, m), 7.78–7.80(1H, m), 8.46(1H, s), 9.48(1H, d, J=7.3 Hz)

Example 53

Ethyl 8-(3-carbamoylphenyl)-1-cyclopropyl-9-methyl-4-oxo-4H-quinolizine-3-carboxylate $^1$H-NMR(CDCl$_3$) δ: 0.76–0.79(2H, m), 1.02–1.05(2H, m), 1.40(3H, t, J=7.11 Hz), 2.26–2.32(1H, m), 2.79(3H, s), 4.37(2H, q, J=7.1 Hz), 7.07(1H, d, J=7.3 Hz), 7.52–7.64(2H, m), 7.99–8.05(2H, m), 8.35(1H, m), 9.36(1H, d, J=7.3 Hz)

Example 54

Ethyl 8-(4-carbamoylphenyl)-1-cyclopropyl-9-methyl-4-oxo-4H-quinolizine-3-carboxylate $^1$H-NMR(CDCl$_3$) δ: 0.78–0.82(2H, m), 1.03–1.07(2H, m), 1.44(3H, t, J=7.1 Hz), 2.35–2.38(1H, m), 2.81(3H, s), 4.44(2H, q, J=7.1 Hz), 7.06(1H, d, J=7.3 Hz), 7.49(2H, d, J=8.3 Hz), 7.97(2H, d, J=8.3 Hz), 8.44(1H, s), 9.48(1H, d, J=7.3 Hz)

Example 55

54 mg of ethyl 8-(4-aminophenyl)-1-cyclopropyl-9-methyl-4-oxo-4H-quinolizine-3-carboxylate (Example 2) was dissolved in a mixture of 3 ml of acetic acid and 2 ml of water. 2 ml of an aqueous solution of 19 mg of sodium cyanate was added to the obtained solution at 35° C. and they were stirred at that temperature for 3 hours. The reaction mixture was poured into a saturated aqueous sodium hydrogencarbonate solution. After the extraction with chloroform, the organic layer was dried over anhydrous sodium sulfate. The solvent was evaporated under reduced pressure, and the residue was purified by the silica gel column chromatography (eluent: chloroform/methanol=20/1) to obtain 53 mg of ethyl 1-cyclopropyl-9-methyl-4-oxo-8-(4-ureidophenyl)-4H-quinolizine-3-carboxylate.

$^1$H-NMR(CD$_3$OD) δ: 0.75–0.79(2H, m), 1.07–1.12(2H, m), 1.41(3H, t, J=7.1 Hz), 2.42–2.49(1H, m), 2.90(3H, s), 4.38(2H, q, J=7.1 Hz), 7.31(1H, d, J=7.6 Hz), 7.39–7.42(2H, m), 7.56–7.60(2H, m), 8.39(1H, s), 9.42(1H, d, J=7.6 Hz)

Example 56

327 mg of ethyl 1-cyclopropyl-8-(4-hydroxymethylphenyl)-9-methyl-4-oxo-4H-quinolizine-3-carboxylate (Example 51) was dissolved in 11 ml of dichloromethane. 380 mg of carbon tetrabromide was added to the obtained solution, and they were cooled to 0° C. 355 mg of triphenylphosphine was added to the reaction mixture, and they were stirred for 30 minutes. The reaction mixture was concentrated under reduced pressure. The obtained residue was purified by the silica gel column chromatography (eluent: hexane/ethyl acetate=1/1) to obtain 291 mg of ethyl 8-(4-bromomethylphenyl)-1-cyclopropyl-9-methyl-4-oxo-4H-quinolizine-3-carboxylate.

$^1$H-NMR(CDCl$_3$) δ: 0.77–0.81(2H, m), 1.02–1.06(2H, m), 1.44(3H, t, J=7.1 Hz), 2.34–2.38(1H, m), 2.82(3H, s), 4.43(2H, q, J=7.1 Hz), 4.57(2H, s), 7.07(1H, d, J=7.6 Hz), 7.38(2H, d, J=8.0 Hz), 7.54(2H, d, J=8.0 Hz), 8.42(1H, s), 9.46(1H, d, J=7.6 Hz)

Example 57

The following compound was synthesized by the same process as that in Example 56:

Ethyl 8-(3-bromomethylphenyl)-1-cyclopropyl-9-methyl-4-oxo-4H-quinolizine-3-carboxylate $^1$H-NMR(CDCl$_3$) δ: 0.78–0.82(2H, m), 1.02–1.07(2H, m), 1.44(3H, t, J=7.1 Hz), 2.33–2.42(1H, m), 2.83(3H, s), 4.44(2H, q, J=7.1 Hz), 4.57(2H, s), 7.09(1H, d, J=7.3 Hz), 7.32–7.34(1H, m), 7.43(1H, d, J=1.0 Hz), 7.49–7.50(2H, m), 8.42(1H, s), 9.48(1H, d, J=7.3 Hz)

Example 58

31.2 mg of ethyl 8-(3-bromomethylphenyl)-1-cyclopropyl-9-methyl-4-oxo-4H-quinolizine-3-carboxylate (Example 57) was dissolved in 2 ml of tetrahydrofuran. 0.1 ml of a solution of 2.0 M of methylamine in tetrahydrofuran was added to the obtained solution, and they were stirred for 10 hours. The reaction mixture was concentrated under reduced pressure. The obtained residue was purified by the silica gel column chromatography (eluent: chloroform/methanol=5/1) to obtain 18.1 mg of ethyl 1-cyclopropyl-9-methyl-8-(3-methylaminomethylphenyl)-4-oxo-4H-quinolizine-3-carboxylate.

1H-NMR(CDCl$_3$) δ: 0.71–0.75(2H, m), 1.03–1.08(2H, m), 1.39(3H, t, J=7.1 Hz), 2.28–2.34(1H, m), 2.75(3H, s), 2.80(3H, s), 4.23(2H, s), 4.36(2H, q, J=7.1 Hz), 7.09(1H, d, J=7.3 Hz), 7.32(1H, d, J=7.8 Hz), 7.48(1H, dd, J=7.6 Hz, 7.8 Hz), 7.62(1H, d, J=7.6 Hz), 7.78(1H, s), 8.30(1H, s), 9.33 (1H, d, J=7.3 Hz)

Example 59

The following compound was synthesized by the same process as that in Example 58:

Ethyl 1-cyclopropyl-9-methyl-8-(4-methylaminomethylphenyl)-4-oxo-4H-quinolizine-3-carboxylate $^1$H-NMR(CDCl$_3$) δ: 0.74–0.83(2H, m), 1.03–1.07(2H, m), 1.42(3H, t, J=7.1 Hz), 2.31–2.38(1H, m), 2.72(3H, s), 2.79(3H, s), 4.16(2H, s), 4.40(2H, q, J=7.1 Hz), 7.03–7.08 (1H, m), 7.35–7.41(2H, m), 7.68–7.73(2H, m), 8.38(1H, s), 9.29–9.33(1H, m)

Example 60

Ethyl 1-cyclopropyl-8-(4-cyclopropylaminomethylphenyl)-9-methyl-4-oxo-4H-quinolizine-3-carboxylate $^1$H-NMR(CDCl$_3$) δ: 0.41–0.51(4H, m), 0.77–0.81(2H, m), 1.01–1.06(2H, m), 1.44(3H, t, J=7.1 Hz), 2.20–2.25(1H, m), 2.33–2.40(1H, m), 2.82(3H, s), 3.93(2H, s), 4.43(2H, q, J=7.1 Hz), 7.10(1H, d, J=7.3 Hz), 7.35(2H, d, J=8.3 Hz), 7.46(2H, d, J=8.3 Hz), 8.41(1H, s), 9.46(1H, d, J=7.3 Hz)

Example 61

The following compound was synthesized by the same process as that in Example 24:

8-(3-Aminomethylphenyl)-1-cyclopropyl-9-methyl-4-oxo-4H-quinolizine-3-carboxylic acid $^1$H-NMR(CF$_3$ COOD) δ: 1.22–1.24(2H, m), 1.56–1.58 (2H, m), 2.80–2.90(1H, m), 3.32(3H, s), 4.74(2H, s), 7.81–7.82(1H, m), 7.91–7.92(3H, m), 8.11(1H, d, J=7.3 Hz), 8.89(1H, s), 9.62(1H, d, J=7.3 Hz) FAB-MS m/z: 349(M+H)$^+$

Example 62

The following compound was synthesized by the same process as that in Example 26:

1-Cyclopropyl-8-(5-formylthiophen-2-yl)-9-methyl-4-oxo-4H-quinolizine-3-carboxylic acid $^1$H-NMR(CDCl$_3$) δ: 0.83–0.89(2H, m), 1.11–1.16(2H, m), 2.38–2.45(1H, m), 3.05(3H, s), 7.33(1H, d, J=7.6 Hz), 7.42(1H, d, J=3.9 Hz), 7.87(1H, d, J=3.9 Hz), 8.63(1H, s), 9.34(1H, d, J=7.6 Hz), 10.01(1H, s) FAB-MS m/z: 354(M+H)$^+$

Example 63

8-(3-Amino-4-methylphenyl)-1-cyclopropyl-9-methyl-4-oxo-4H-quinolizine-3-carboxylic acid $^1$H-NMR(CDCl$_3$) δ: 0.81–0.86(2H, m), 1.06–1.11(2H, m), 2.26(3H, s), 2.38–2.44(1H, m), 2.90(3H, s), 6.68–6.72 (2H, m), 7.18–7.29(2H, m), 8.56(1H, s), 9.34(1H, d, J=7.3 Hz)

Example 64

8-[4-(2-Amino-2-carboxyethyl)phenyl]-1-cyclopropyl-9-methyl-4-oxo-4H-quinolizine-3-carboxylic acid $^1$H-NMR(CF$_3$ COOD) δ: 1.26–1.30(2H, m), 1.62–1.67 (2H, m), 2.89–2.96(1H, m), 3.39(3H, s), 3.79(1H, dd, J=8.8, 15.1 Hz), 4.02(1H, dd, J=4.6, 15.1 Hz), 5.04–5.07(1H, m), 7.83–7.91(4H, m), 8.17(1H, d, J=7.3 Hz), 8.96(1H, s), 9.69(1H, d, J=7.3 Hz) FAB-MS m/z: 407(M+H)$^+$

Example 65

1-Cyclopropyl-9-methyl-4-oxo-8-(4-ureidophenyl)-4H-quinolizine-3-carboxylic acid $^1$H-NMR(CF$_3$ COOD) δ: 1.25–1.30(2H, m), 1.61–1.66 (2H, m), 2.88–2.95(1H, m), 3.39(3H, s), 7.85–7.88(4H, m), 8.15–8.16(1H, m), 8.94(1H, s), 8.67–9.68(1H, m)

Example 66

1-Cyclopropyl-8-(4-hydroxymethylphenyl)-9-methyl-4-oxo-4H-quinolizine-3-carboxylic acid $^1$H-NMR(CDCl$_3$) δ: 0.85–0.86(2H, m), 1.09–1.11(2H, m), 1.84(1H, m), 2.40–2.43(1H, m), 2.89(3H, s), 4.82–4.84

(2H, m), 7.26–7.27(1H, m), 7.41(2H, d, J=8.3 Hz), 7.55(2H, d, J=8.3 Hz), 8.60(1H, s), 9.39(1H, d, J=7.3 Hz), 14.07(1H, s) FAB-MS m/z: 350(M+H)⁺

Example 67

1-Cyclopropyl-9-methyl-8-(3-methylaminomethylphenyl)-4-oxo-4H-quinolizine-3-carboxylic acid ¹H-NMR(CDCl₃) δ: 0.81–0.85(2H, m), 1.08–1.13(2H, m), 2.31–2.42(1H, m), 2.65(3H, s), 2.90(3H, s), 4.23(2H, s), 7.41(1H, d, J=7.6 Hz), 7.49(1H, d, J=8.1 Hz), 7.59(1H, dd, J=7.6 Hz, 8.1 Hz), 7.70(1H, d, J=7.6 Hz), 7.80(1H, s), 8.46(1H, s), 9.25(1H, d, J=7.3 Hz) FAB-MS m/z: 363(M+H)⁺

Example 68

1-Cyclopropyl-9-methyl-8-(4-methylaminomethylphenyl)-4-oxo-4H-quinolizine-3-carboxylic acid ¹H-NMR(CF₃COOD) δ: 1.21–1.23(2H, m), 1.57–1.59(2H, m), 2.86(1H, m), 3.24(3H, s), 3.31(3H, s), 4.69(2H, s), 7.82–8.09(5H, m), 8.90(1H, s), 9.63(1H, d, J=7.1 Hz) FAB-MS m/z: 363(M+H)⁺

Example 69

8-(3-Carbamoylphenyl)-1-cyclopropyl-9-methyl-4-oxo-4H-quinolizine-3-carboxylic acid ¹H-NMR(CF₃COOD) δ: 1.23–1.24(2H, m), 1.57–1.59(2H, m), 2.79–2.88(1H, m), 3.32(3H, s), 8.02–8.03(2H, m), 8.11(1H, s), 8.33–8.35(2H, m), 8.91(1H, s), 9.64(1H, d, J=7.3 Hz) FAB-MS m/z: 363(M+H)⁺

Example 70

8-(4-Carbamoylphenyl)-1-cyclopropyl-9-methyl-4-oxo-4H-quinolizine-3-carboxylic acid ¹H-NMR(CF₃COOD) δ: 1.23–1.25(2H, m), 1.59–1.62(2H, m), 2.83–2.89(1H, m), 3.33(3H, s), 7.92(2H, d, J=8.3 Hz), 8.09(1H, d, J=8.3 Hz), 8.43(2H, d, J=8.3 Hz), 8.94(1H, s), 9.66(1H, d, J=7.3 Hz) FAB-MS m/z: 363(M+H)⁺

Example 71

8-(3-Cyanophenyl)-1-cyclopropyl-9-methyl-4-oxo-4H-quinolizine-3-carboxylic acid

¹H-NMR(CDCl₃) δ: 0.85–0.89(2H, m), 1.11–1.15(2H, m), 2.38–2.45(1H, m), 2.88(3H, s), 7.21(1H, d, J=7.3 Hz), 7.65–7.72(3H, m), 7.80–7.83(1H, m), 8.64(1H, s), 9.41(1H, d, J=7.3 Hz) FAB-MS m/z: 345(M+H)⁺

Example 72

1-Cyclopropyl-8-(4-cyclopropylaminomethylphenyl)-9-methyl-4-oxo-4H-quinolizine-3-carboxylic acid ¹H-NMR(CF₃COOD) δ: 1.35–1.48(6H, m), 1.69–1.71(2H, m), 2.99(1H, brs), 3.29(1H, brs), 3.44(3H, s), 4.93(2H, s), 7.96(3H, brs), 8.10(2H, brs), 8.21(1H, brs), 9.03(1H, s), 9.76(1H, brs) FAB-MS m/z: 389(M+H)⁺

Example 73

The following compound was synthesized by the same process as that in Example 1:

Ethyl 8-[4-(2-tert-butoxycarbonylaminoethyl)phenyl]-1-cyclopropyl-9-methyl-4-oxo-4H-quinolizine-3-carboxylate ¹H-NMR(CDCl₃) δ: 0.76–0.80(2H, m), 1.02–1.07(2H, m), 1.42–1.45(12H, m), 2.34–2.41(1H, m), 2.84(3H, s), 2.89–2.93(2H, m), 3.43–3.48(2H, m), 4.43(2H, q, J=7.1 Hz), 4.95(1H, brs), 7.10(1H, d, J=7.6 Hz), 7.34–7.36(4H, m), 8.41(1H, s), 9.46(1H, d, J=7.6 Hz)

Example 74

The following compound was synthesized by the same process as that in Example 47:

8-[4-(2-Aminoethyl)phenyl]-1-cyclopropyl-9-methyl-4-oxo-4H-quinolizine-3-carboxylic acid ¹H-NMR(CD₃OD) δ: 0.81–0.85(2H, m), 1.10–1.15(2H, m), 2.49–2.56(1H, m), 2.93(3H, s), 3.08(2H, t, J=8.6 Hz), 3.25–3.31(2H, m), 7.45(1H, d, J=7.3 Hz), 7.50–7.55(4H, m), 8.42(1H, s), 9.41(1H, d, J=7.3 Hz)

Example 75

The following compound was synthesized by the same process as that in Example 15:

Ethyl 1-cyclopropyl-8-[5-(hydroxymethyl)thiophen-2-yl]-9-methyl-4-oxo-4H-quinolizine-3-carboxylate ¹H-NMR(CDCl₃) δ: 0.72–0.76(2H, m), 1.02–1.06(2H, m), 1.44(3H, t, J=7.1 Hz), 2.31–2.37(1H, m), 2.97(3H, s), 4.43(2H, q, J=7.1 Hz), 4.91(2H, s), 7.05(1H, d, J=3.4 Hz), 7.13(1H, d, J=7.3 Hz), 7.16(1H, d, J=3.4 Hz), 8.39(1H, s), 9.32(1H, d, J=7.3 Hz)

Example 76

The following compound was synthesized by the same process as that in Example 56:

Ethyl 8-[3-(1-bromoethyl)phenyl]-1-cyclopropyl-9-methyl-4-oxo-4H-quinolizine-3-carboxylate ¹H-NMR(CDCl₃) δ: 0.78–0.82(2H, m), 1.02–1.07(2H, m), 1.44(3H, t, J=7.3 Hz), 2.10(3H, d, J=6.8 Hz), 2.83(3H, s), 4.44(2H, q, J=7.3 Hz), 5.27(1H, q, J=6.8 Hz), 7.10(1H, d, J=7.6 Hz), 7.31–7.33(1H, m), 7.46–7.55(3H, m), 8.42(1H, s), 9.48(1H, d, J=7.6 Hz)

Example 77

Ethyl 8-[4-(1-bromoethyl)phenyl]-1-cyclopropyl-9-methyl-4-oxo-4H-quinolizine-3-carboxylate ¹H-NMR(CDCl₃) δ: 0.78–0.82(2H, m), 1.02–1.07(2H, m), 1.44(3H, t, J=7.1 Hz), 2.11(3H, d, J=6.8 Hz), 2.34–2.41(1H, m), 2.84(3H, s), 4.44(2H, q, J=7.1 Hz), 5.28(1H, q, J=6.8 Hz), 7.10(1H, d, J=7.6 Hz), 7.38(2H, d, J=8.1 Hz), 7.59(2H, d, J=8.1 Hz), 8.42(1H, s), 9.47(1H, d, J=7.6 Hz)

Example 78

Ethyl 8-[5-(bromomethyl)thiophen-2-yl]-1-cyclopropyl-9-methyl-4-oxo-4H-quinolizine-3-carboxylate $^1$H-NMR(CDCl$_3$) δ: 0.73–0.78(2H, m), 1.02–1.07(2H, m), 1.43(3H, t, J=7.1 Hz), 2.32–2.38(1H, m), 2.99(3H, S), 4.43(2H, q, J=7.1 Hz), 4.77(2H, s), 7.15–7.27(31H, m), 8.41(1H, s), 9.38(1H, d, J=7.6 Hz)

Example 79

46.1 mg of ethyl 8-[3-(1-bromoethyl)phenyl]-1-cyclopropyl-9-methyl-4-oxo-4H-quinolizine-3-carboxylate was dissolved in 2 ml of tetrahydrofuran. 0.1 ml of a solution of 2.0 M of methylamine in tetrahydrofuran was added to the obtained solution and they were stirred for 10 hours. The reaction mixture was concentrated under reduced pressure, and the obtained residue was dissolved in 1 N hydrochloric acid. After washing the obtained solution with ethyl acetate, the aqueous layer was concentrated under reduced pressure. The obtained residue was dissolved in 2 ml of methanol. 1 ml of 1 N aqueous sodium hydroxide solution was added to the obtained solution, and they were stirred at 50° C. for 1 hour. The reaction mixture was made acidic with 1 N hydrochloric acid to obtain 8.1 mg of 1-cyclopropyl-9-methyl-8-[3-(1-methylaminoethyl)phenyl]-4-oxo-4H-quinolizine-3-carboxylic acid in the form of crystals.

$^1$H-NMR(CF$_3$COOD) δ: 1.43–1.47(2H, m), 1.77–1.82 (2H, m), 2.32(3H, d, J=6.6 Hz), 3.03–3.10(1H, m), 3.30(3H, s), 3.54(3H, s), 5.00–5.02(1H, m), 8.05–8.20(4H, m), 8.33 (1H, d, J=7.3 Hz), 9.11(1H, s), 9.85(1H, d, J=7.3 Hz)

Example 80

The following corresponding amino compounds were synthesized with various amine reagents by the same process as that in Example 56:

8-[3-(1-aminoethyl)phenyl]-1-cyclopropyl-9-methyl-4-oxo-4H-quinolizine-3-carboxylic acid $^1$H-NMR(CF$_3$COOD) δ: 1.27–1.28(2H, m), 1.61–1.63 (2H, m), 2.15(3H, d, J=6.1 Hz), 2.86–2.94(1H, m), 3.36(3H, s), 5.11(1H, brs), 7.86–7.98(4H, m), 8.14(1H, d, J=6.8 Hz), 8.94(1H, s), 9.67(1H, d, J=6.8 Hz)

Example 81

1-Cyclopropyl-8-[3-(1-cyclopropylaminoethyl)phenyl]-9-methyl-4-oxo-4H-quinolizine-3-carboxylic acid $^1$H-NMR(CF$_3$COOD) δ: 1.09–1.22(6H, m), 1.48–1.50 (2H, m), 2.05(3H, d, J=6.3 Hz), 2.73–2.79(1H, m), 2.86–2.92(1H, m), 3.23(3H, s), 4.85–4.90(1H, m), 7.74–7.85(4H, m), 8.01(1H, d, J=7.3 Hz), 8.80(1H, s), 9.54(1H, d, J=7.3 Hz)

Example 82

8-[4-(1-aminoethyl)phenyl]-1-cyclopropyl-9-methyl-4-oxo-4H-quinolizine-3-carboxylic acid $^1$H-NMR(CF$_3$COOD) δ: 1.17–1.20(2H, m), 1.53–1.57 (2H, m), 2.07(3H, d, J=6.3 Hz), 2.82(1H, brs), 3.28(3H, s), 5.03(1H, brs), 7.78(2H, d, J=7.1 Hz), 7.92(2H, d, J=7.1 Hz), 8.04(1H, d, J=6.8 Hz), 8.86(1H, s), 9.59(1H, d, J=6.8 Hz)

Example 83

1-Cyclopropyl-8-[3-(cyclopropylaminomethyl)phenyl]-9-methyl-4-oxo-4H-quinolizine-3-carboxylic acid $^1$H-NMR(CF$_3$COOD) δ: 1.27–1.36(6H, m), 1.61–1.63 (2H, m), 2.86–2.92(1H, m), 3.16–3.23(1H, m), 3.36(3H, s), 4.84(2H, s), 7.87–7.98(4H, m), 8.13(1H, d, J=7.1 Hz), 8.94(1H, s), 9.67(1H, d, J=7.1 Hz)

Example 84

8-[5-(Aminomethyl)thiophen-2-yl]-1-cyclopropyl-9-methyl-4-oxo-4H-quinolizine-3-carboxylic acid $^1$H-NMR(CF$_3$COOD) δ: 1.13–1.18(2H, m), 1.53–1.59 (2H, m), 2.77–2.84(1H, m), 3.46(3H, s), 4.90(2H, s), 7.65 (1H, d, J=3.5 Hz), 7.71(1H, d, J=3.5 Hz), 8.14(1H, d, J=7.6 Hz), 8.85(1H, s), 9.51(1H, d, J=7.6 Hz)

Example 85

1-Cyclopropyl-9-methyl-8-[5-(methylaminomethyl)thiophen-2-yl]-4-oxo-4H-quinolizine-3-carboxylic acid $^1$H-NMR(CF$_3$COOD) δ: 1.21–1.25(2H, m), 1.60–1.65 (2H, m), 2.84–2.91(1H, m), 3.29(3H, s), 3.52(3H, s), 4.93 (2H, s), 7.73(1H, d, J=3.2 Hz), 7.79(1H, d, J=3.2 Hz), 8.21(1H, d, J=7.3 Hz), 8.92(1H, s), 9.58(1H, d, J=7.3 Hz)

Example 86

1-Cyclopropyl-8-[5-(cyclopropylaminomethyl)thiophen-2-yl]-9-methyl-4-oxo-4H-quinolizine-3-carboxylic acid $^1$H-NMR(CF$_3$COOD) δ: 1.09–1.13(2H, m), 1.21–1.26 (4H, m), 1.48–1.53(2H, m), 2.72–2.78(1H, m), 3.10–3.15 (1H, m), 3.39(3H, s), 4.91(2H, s), 7.60(1H, d, J=3.7 Hz), 7.66(1H, d, J=3.7 Hz), 8.08(1H, d, J=7.3 Hz), 8.80(1H, s), 9.46(1H, d, J=7.3 Hz)

Example 87

8-[4-(2-Aminoethylamino)phenyl]-1-cyclopropyl-9-methyl-4-oxo-4H-quinolizine-3-carboxylic acid was synthesized from ethyl 1-cyclopropyl-9-methyl-4-oxo-8-{4-[2-(tetrahydropyran-2-yloxy)ethylamino]phenyl}-4H-quinolizine-3-carboxylate in the same manner as that in Example 46 and then Examples 56 and 79.

$^1$H-NMR(CF$_3$COOD) δ: 1.16–1.20(2H, m), 1.51–1.56 (2H, m), 2.77–2.84(1H, m), 3.25(3H, s), 4.12–4.15(2H, m), 4.42–4.45(2H, m), 7.91–8.05(5H, m), 8.89(1H, s), 9.61(1H, d, J=7.3 Hz) FAB-MS m/z: 378(M+H)$^+$

Referential Example 1

1.00 g of ethyl 8-chloro-1-cyclopropyl-9-methyl-4-oxo-4H-quinolizine-3-carboxylate was dissolved in 20 ml of toluene. 4.96 ml of bis[tributyltin (IV)] and 230 mg of bis(triphenylphosphine)palladium (II) chloride were added to the obtained solution, and they were heated under reflux in argon atmosphere for 3 hours. After the completion of the reaction, the solvent was evaporated under reduce pressure, and the obtained residue was purified by the silica gel column chromatography (eluent: hexane/ethyl acetate=4/1) to obtain 0.48 g of ethyl 1-cyclopropyl-9-methyl-4-oxo-8-tributylstannyl-4H-quinolizine-3-carboxylate.

$^1$H-NMR(CDCl$_3$) δ: 0.72–0.76(2H, m), 0.89–1.64(32H, m), 2.31–2.40(1H, m), 3.05(3H, s), 4.42(2H, q, J=7.3 Hz), 7.21(1H, d, J=7.1 Hz), 8.37(1H, s), 9.34(1H, d, J=7.1 Hz)

Referential Example 2

3.20 g of 2-amino-5-bromopyridine was dissolved in 10 ml of dichloromethane. 5.61 g of triethylamine and 4.44 g of di-tert-butyl dicarbonate were added to the obtained solution, and they were stirred at room temperature in argon atmosphere for 17 hours. After the completion of the reaction, the precipitates were separated by the filtration, and the solvent was evaporated under reduced pressure. The obtained residue was purified by the silica gel column chromatography (eluent: hexane/ethyl acetate=19/1) to obtain 0.93 g of tert-butyl (5-bromopyridin-2-yl)carbamate.

$^1$H-NMR(CDCl$_3$) δ: 1.57(9H, s), 7.74–7.77(1H, m), 7.96 (1H, d, J=9.0 Hz), 8.40–8.41(1H, m), 9.19(1H, s)

Example 88

73 mg of tert-butyl (5-bromopyridin-2-yl)carbamate was dissolved in 1 ml of DMF. 62 mg of silver (I) oxide and 31 mg of tetrakis(triphenylphosphine)palladium were added to the obtained solution, and they were stirred at 100° C. in argon atmosphere for 5 minutes. 1 ml of a solution of 100 mg of ethyl 1-cyclopropyl-9-methyl-4-oxo-8-tributylstannyl-4H-quinolizine-3-carboxylate in DMF was added dropwise to the reaction mixture, and they were stirred at that temperature for 1 hour. The reaction mixture was poured into water. After the extraction with chloroform, the organic layer was washed with water and then dried over anhydrous sodium sulfate. The solvent was evaporated under reduced pressure, and the obtained residue was purified by the silica gel column chromatography (eluent: hexane/ethyl acetate=1/1) to obtain 11 mg of ethyl 8-(6-tert-butoxycarbonylaminopyridin-3-yl)-1-cyclopropyl-9-methyl-4-oxo-4H-quinolizine-3-carboxylate.

$^1$H-NMR(CDCl$_3$) δ: 0.78–1.46(16H, m), 2.30–2.40(1H, m), 3.04(3H, s), 4.40–4.45(2H, m), 7.05–7.70(4H, m), 8.36 (1H, s), 9.50(1H, d, J=7.1 Hz)

Example 89

The following compound (Example 89) was synthesized by the same process as that in Example 26:

8-(6-Aminopyridin-3-yl)-1-cyclopropyl-9-methyl-4-oxo-4H-quinolizine-3-carboxylic acid $^1$H-NMR(CDCl$_3$) δ: 0.81–0.86(2H, m), 1.08–1.12(2H, m), 2.37–2.45(1H, m), 2.93(3H, s), 4.74(2H, s), 6.66(1H, d, J=8.3 Hz), 7.23–7.30(1H, m), 7.52–7.56(1H, m), 8.20(1H, d, J=2.2 Hz), 8.59(1H, s), 9.37(1H, d, J=7.6 Hz) FAB-MS m/z: 336(M+H)$^+$ Example 90

The following compounds (Example 90–93) were synthesized by the same process as that in Example 1:

Ethyl 8-{4-[(tert-butoxycarbonylmethylamino)methyl]-3-fluorophenyl}-1-cyclopropyl-9-methyl-4-oxo-4H-quinolizine-3-carboxylate $^1$H-NMR(CDCl$_1$) δ: 0.77–0.82(2H, m), 1.02–1.07(2H, m), 1.41–1.50(12H, m), 2.33–2.38(1H, m), 2.83(3H, s), 2.94(3H, s), 4.41–4.56(4H, m), 7.05–7.70(4H, m), 8.42(1H, s), 9.46(1H, d, J=7.3 Hz)

Example 91

Ethyl 8-(4-amino-3-fluorophenyl)-1-cyclopropyl-9-methyl-4-oxo-4H-quinolizine-3-carboxylate $^1$H-NMR(CDCl$_3$) δ: 0.74–0.78(2H, m), 1.01–1.06(2H, m), 1.42–1.48(3H, m), 2.32–2.38(1H, m), 2.85(3H, s), 4.03–4.46(4H, m), 6.88–7.10(4H, m), 8.40(1H, s), 9.43(1H, d, J=7.6 Hz)

Example 92

Ethyl 1-cyclopropyl-9-methyl-4-oxo-8-{4-[(tritylamino)methyl] thiophen-2-yl}-4H-quinolizine-3-carboxylate $^1$H-NMR(CDCl$_3$) δ: 0.73–0.77(2H, m), 1.02–1.07(2H, m), 1.43(3H, t, J=7.1 Hz), 2.32–2.38(1H, m), 2.99(3H, s), 3.40(2H, s), 4.38–4.45(2H, m), 7.18–7.57(18H, m), 8.40 (1H, s), 9.39(1H, d, J=7.6 Hz)

Example 93

Ethyl 1-cyclopropyl-8-{4-fluoro-3-[(tritylamino) methyl]phenyl}-9-methyl-4-oxo-4H-quinolizine-3-carboxylate $^1$H-NMR(CDCl$_3$) δ: 0.79–0.83(2H, m), 1.04–1.08(2H, m), 1.45(3H, t, J=7.1 Hz), 2.35–2.42(1H, m), 2.87(3H, s), 3.44(2H, s), 4.45(2H, q, J=7.1 Hz), 7.11–7.61(19H, m), 8.44(1H, s), 9.50(1H, d, J=7.3 Hz)

Example 94

The following compounds (Example 94–96) were synthesized by the same process as that in Example 47:

1-Cyclopropyl-8-(3-fluoro-4-methylaminomethylphenyl)-9-methyl-4-oxo-4H-quinolizine-3-carboxylic acid $^1$H-NMR(CF$_3$COOD) δ: 2.00–2.04(2H, m), 2.35–2.40 (2H, m), 3.61–3.68(1H, m), 4.06(3H, s), 4.11(3H, s), 5.56 (2H, s), 8.37–8.43(2H, m), 8.76–8.86(2H, m), 9.73(1H, s), 10.43(1H, d, J=7.1 Hz) FAB-MS m/z: 381(M+H)$^+$ Example 95

8-(4-Aminomethylthiophen-2-yl)-1-cyclopropyl-9-methyl-4-oxo-4H-quinolizine-3-carboxylic acid $^1$H-NMR(CF$_3$COOD) δ: 2.08–2.12(2H, m), 2.48–2.53 (2H, m), 3.72–3.78(1H, m), 4.41(3H, s), 5.65(2H, s), 8.83

(1H, s), 9.07–9.11(2H, m), 9.79(1H, s), 10.45(1H, d, J=7.6 Hz) FAB-MS m/z: 355(M+H)$^+$

Example 96

8-(3-Aminomethyl-4-fluorophenyl)-1-cyclopropyl-9-methyl-4-oxo-4H-quinolizine-3-carboxylic acid $^1$H-NMR(CF$_3$COOD) δ: 1.42–1.43(2H, m), 1.77–1.79 (2H, m), 3.01–3.08(1H, m), 3.52(3H, s), 5.02(2H, s), 7.84–8.27(4H, m), 9.11(1H, s), 9.82(1H, d, J=7.3 Hz) FAB-MS m/z: 367(M+H)$^+$

Example 97

The following compound (Example 97) was synthesized by the same process as that in Example 26:

8-(4-amino-3-fluorophenyl)-1-cyclopropyl-9-methyl-4-oxo-4H-quinolizine-3-carboxylic acid $^1$H-NMR(CF$_3$COOD) δ: 1.18–1.24(2H, m), 1.53–1.58 (2H, m), 2.78–2.86(1H, m), 3.28(3H, s), 7.66–8.10(4H, m), 8.93(1H, s), 9.63(1H, d, J=7.1 Hz) FAB-MS m/z: 353(M+H)$^+$

Example 98

The following compounds (Examples 98–104) were synthesized by the same process as that in Example 1:

Ethyl 1-cyclopropyl-9-methoxy-4-oxo-8-{3-[(tritylamino)methyl]phenyl}-4H-quinolizine-3-carboxylate $^1$H-NMR(CDCl$_3$) δ: 0.75–0.80(2H, m), 0.96–1.01(2H, m), 1.44(3H, t, J=7.1 Hz), 2.55–2.62(1H, m), 3.45(2H, s), 3.48(3H, s), 4.44(2H, q, J=7.1 Hz), 7.20–7.33(10H, m), 7.47–7.62(9H, m), 7.73(1H, s), 8.27(1H, s), 9.40(1H, d, J=7.6 Hz)

Example 99

Ethyl 1-cyclopropyl-8-(5-formylthiophen-2-yl)-9-methoxy-4-oxo-4H-quinolizine-3-carboxylate $^1$H-NMR(CDCl$_3$) δ: 0.76–0.80(2H, m), 1.03–1.08(2H, m), 1.43(3H, t, J=7.1 Hz), 2.60–2.67(1H, m), 3.81(3H, s), 4.44(2H, q, J=7.1 Hz), 7.37(1H, d, J=7.8 Hz), 7.79(1H, d, J=4.1 Hz), 7.84(1H, d, J=4.2 Hz), 8.21(1H, s), 9.28(1H, d, J=7.6 Hz), 10.0(1H, s)

Example 100

Ethyl 1-cyclopropyl-8-(5-formylfuran-2-yl)-9-methyl-4-oxo-4H-quinolizine-3-carboxylate $^1$H-NMR(CDCl$_8$) δ: 0.73–0.77(2H, m), 1.06–1.11(2H, m), 1.44(3H, t, J=7.1 Hz), 2.33–2.40(1H, m), 3.07(3H, s), 4.29(2H, q, J=7.1 Hz), 7.05(1H, d, J=3.9 Hz), 7.42–7.46(2H, m), 8.43(1H, s), 9.40(1H, d, J=7.6 Hz), 9.79(1H, s)

Example 101

Ethyl 1-cyclopropyl-8-[4-fluoro-5-(tetrahydropyran-2-yloxy)thiophen-2-yl]-9-methyl-4-oxo-4H-quinolizine-3-carboxylate $^1$H-NMR(CDCl$_3$) δ: 0.73–0.77(2H, m), 1.03–1.08(2H, m), 1.43(3H, t, J=7.1 Hz), 1.56–1.90(6H, m), 2.32–2.39(1H, m), 3.00(3H, s), 3.58–3.62(1H, m), 3.90–3.96(1H, m), 4.43 (2H, q, J=7.1 Hz), 4.73(1H, d, J=12.9 Hz), 4.80–4.81(1H, m), 4.89(1H, d, J=13.4 Hz), 7.03(1H, s), 7.14(1H, d, J=7.5 Hz), 8.42(1H, s), 9.38(1H, d, J=7.6 Hz)

Example 102

The following compound was synthesized by the same process as that in Example 15:

Ethyl 1-cyclopropyl-8-(5-hydroxymethylthiophen-2-yl)-9-methoxy-4-oxo-4H-quinolizine-3-carboxylate $^1$H-NMR(CDCl$_3$) δ: 0.74–0.78(2H, m), 1.00–1.04(2H, m), 1.43(3H, t, J=7.1 Hz), 2.05(1H, brs), 2.59–2.64(1H, m), 3.77(3H, s), 4.43(2H, q, J=7.1 Hz), 4.93(2H, d, =6.1 Hz), 7.08(1H, d, J=3.9 Hz), 7.37(1H, d, J=7.8 Hz), 7.62(1H, d, J=2.7 Hz), 8.18(1H, s), 9.25(1H, d, J=7.8 Hz)

Example 103

Ethyl 1-cyclopropyl-8-(5-hydroxymethylfuran-2-yl)-9-methyl-4-oxo-4H-quinolizine-3-carboxylate $^1$H-NMR(CDCl$_3$) δ: 0.70–0.74(2H, m), 1.02–1.07(2H, m), 1.43(3H, t, J=7.3 Hz), 2.31–2.38(1H, m), 3.00(3H, s), 4.43(2H, q, J=7.3 Hz), 4.76(2H, s), 6.55(1H, d, J=3.4 Hz), 6.87(1H, d, J=3.7 Hz), 7.48(1H, d, J=7.6 Hz), 8.37(1H, s), 9.37(1H, d, J=7.6 Hz)

Example 104

318 mg of ethyl 1-cyclopropyl-8-[4-fluoro-5-(tetrahydropyran-2-yloxy)-thiophen-2-yl]-9-methyl-4-oxo-4H-quinolizine-3-carboxylate (Example 101) was dissolved in 5 ml of tetrahydrofuran. 5 ml of ethanol and 43.0 mg of pyridinium p-toluenesulfonate were added to the obtained solution, and they were heated under reflux for 3 hours. The reaction mixture was poured into saturated aqueous sodium hydrogencarbonate solution. After the extraction with ethyl acetate, the organic layer was washed with water and then with saturated aqueous sodium chloride solution, and then dried over anhydrous sodium sulfate. The solvent was evaporated under reduced pressure, and the obtained residue was purified by the silica gel column chromatography (eluent: chloroform/ethyl acetate=5/1) to obtain 230 mg of ethyl 1-cyclopropyl-8-(4-fluoro-5-hydroxymethylthiophen-2-yl)-9-methyl-4-oxo-4H-quinolizine-3-carboxylate.

$^1$H-NMR(CDCl$_3$) δ: 0.73–0.77(2H, m), 1.03–1.08(2H, m), 1.44(3H, t, J=7.1 Hz), 2.31–2.37(1H, m), 2.99(3H, s), 4.43(2H, q, J=7.1 Hz), 4.88(2H, s), 7.02(1H, s), 7.11(1H, d, J=7.3 Hz), 8.42(1H, s), 9.38(1H, d, J=7.6 Hz)

Example 105

The following compounds (Examples 105 to 108) were synthesized by the same process as that in Example 56:

Ethyl 8-(5-bromomethylthiophen-2-yl)-1-cyclopropyl-9-methoxy-4-oxo-4H-quinolizine-3-carboxylate $^1$H-NMR(CDCl$_3$) δ: 0.75–0.79(2H, m), 1.00–1.05(2H, m), 1.43(3H, t, J=7.1 Hz), 2.59–2.66(1H, m), 3.79(3H, s), 4.43(2H, q, J=7.1 Hz), 4.78(2H, s), 7.21(1H, d, J=3.7 Hz), 7.37(1H, d, J=7.8 Hz), 7.60(1H, d, J=3.9 Hz), 8.18(1H, s), 9.26(1H, d, J=7.8 Hz)

Example 106

Ethyl 8-(5-bromomethyl-4-fluorothiophen-2-yl)-1-cyclopropyl-9-methyl-4-oxo-4H-quinolizine-3-carboxylate $^1$H-NMR(CDCl$_3$) δ: 0.74–0.78(2H, m), 1.04–1.08(2H, m), 1.43(3H, t, J=7.1 Hz), 2.32–2.38(1H, m), 2.99(3H, s), 4.43(2H, q, J=7.1 Hz), 4.70(2H, s), 7.00(1H, s), 7.10(1H, d, J=7.5 Hz), 8.43(1H, s), 9.38(1H, d, J=7.6 Hz)

Example 107

Ethyl 8-(5-bromomethylfuran-2-yl)-1-cyclopropyl-9-methyl-4-oxo-4H-quinolizine-3-carboxylate $^1$H-NMR(CDCl$_3$) δ: 0.70–0.74(2H, m), 1.03–1.08(2H, m), 1.43(3H, t, J=7.3 Hz), 2.33–2.39(1H, m), 3.02(3H, s), 4.25(2H, q, J=7.3 Hz), 4.59(2H, s), 6.63(1H, d, J=3.4 Hz), 6.87(1H, d, J=3.4 Hz), 7.46(1H, d, J=7.6 Hz), 8.39(1H, s), 9.39(1H, d, J=7.8 Hz)

Example 108

Ethyl 1-cyclopropyl-8-(4-ethylaminomethylphenyl)-9-methyl-4-oxo-4H-quinolizine-3-carboxylate $^1$H-NMR(CDCl$_3$) δ: 0.78(2H, m), 1.02(2H, m), 1.23(3H, t, J=7.1 Hz), 1.43(3H, t, J=7.1 Hz), 2.34(1H, m), 2.78–2.83 (5H, m), 3.94(2H, m), 4.43(2H, q, J=7.1 Hz), 7.07–7.54(5H, m), 8.41(1H, s), 9.44(1H, d, J=7.5 Hz)

Example 109

The following compounds (Examples 109 to 111) were synthesized by the same process as that in Example 58:

Ethyl 8-(5-aminomethylphenylthiophen-2-yl)-1-cyclopropyl-9-methoxy-4-oxo-4H-quinolizine-3-carboxylate $^1$H-NMR(CDCl$_8$) δ: 0.75–0.78(2H, m), 0.98–1.03(2H, m), 1.43(3H, t, J=7.1 Hz), 2.58–2.64(1H, m), 3.77(3H, s), 4.16(2H, s), 4.43(2H, q, J=7.1 Hz), 7.02(1H, d, J=3.9 Hz), 7.39(1H, d, J=7.8 Hz), 7.63(1H, d, J=3.9 Hz), 8.18(1H, s), 9.27(1H, d, J=7.8 Hz)

Example 110

Ethyl 8-(5-aminomethylfuran-2-yl)-1-cyclopropyl-9-methyl-4-oxo-4H-quinolizine-3-carboxylate $^1$H-NMR(CDCl$_3$) δ: 0.69–0.73(2H, m), 1.02–1.07(2H, m), 1.43(3H, t, J=7.3 Hz), 2.32–2.38(1H, m), 3.01(3H, s), 3.99(2H, s), 4.42(2H, q, J=7.3 Hz), 6.43(1H, d, J=3.2 Hz), 6.87(1H, d, J=3.4 Hz), 7.49(1H, d, J=7.6 Hz), 8.37(1H, s), 9.37(1H, d, J=7.6 Hz)

Example 111

Ethyl 8-(5-aminomethyl-4-fluorothiophen-2-yl)-1-cyclopropyl-9-methyl-4-oxo-4H-quinolizine-3-carboxylate $^1$H-NMR(CDCl$_3$) δ: 0.73–0.76(2H, m), 1.02–1.07(2H, m), 1.41–1.45(3H, m), 2.31–2.38(1H, m), 2.99(3H, s), 4.11 (2H, s), 4.40–4.45(2H, m), 7.01(1H s), 7.13(1H, d, J=7.6 Hz), 8.40(1H, s), 9.36(1H, d, J=7.6 Hz)

Example 112

The following compounds (Examples 112 to 115) were synthesized by the same process as that in Example 26:

8-(5-Aminomethylthiophen-2-yl)-1-cyclopropyl-9-methoxy-4-oxo-4H-quinolizine-3-carboxylic acid $^1$H-NMR(CF$_3$COOD) δ: 1.14–1.18(2H, m), 1.51–1.56 (2H, m), 3.13–3.19(1H, m), 4.14(3H, s), 4.92(2H, s), 7.66 (1H, d, J=3.4 Hz), 8.19(1H, d, J=3.7 Hz), 8.44(1H, d, J=6.8 Hz), 8.60(1H, s), 9.39(1H, d, J=7.6 Hz) FAB-MS m/z: 371(M+H)$^+$

Example 113

8-(5-Aminomethylfuran-2-yl)-1-cyclopropyl-9-methyl-4-oxo-4H-quinolizine-3-carboxylic acid $^1$H-NMR(CF$_3$COOD) δ: 1.01–1.05(2H, m), 1.43–1.48 (2H, m), 2.65–2.72(1H, m), 3.38(3H, s), 4.72(2H, s), 7.03 (1H, d, J=3.7 Hz), 7.42(1H, d, J=3.7 Hz), 8.41(1H, d, J=7.6 Hz), 8.68(1H, s), 9.37(1H, d, J=7.6 Hz) FAB-MS m/z: 339(M+H)$^+$

Example 114

8-(5-Aminomethyl-4-fluorothiophen-2-yl)-1-cyclopropyl-9-methyl-4-oxo-4H-quinolizine-3-carboxylic acid $^1$H-NMR(CF$_3$COOD) δ: 1.14–1.18(2H, m), 1.53–1.58 (2H, m), 2.77–2.83(1H, m), 3.45(3H, s), 4.86(0.3H, s), 7.50(1H, s); 8.08(1H, d, J=7.3 Hz), 8.88(1H, s), 9.52(1H, d, J=7.1 Hz) FAB-MS m/z: 373(M+H)$^+$

Example 115

1-Cyclopropyl-8-(4-ethylaminomethylphenyl)-9-methyl-4-oxo-4H-quinolizine-3-carboxylic acid $^1$H-NMR(CF$_3$COOD) δ: 1.18(2H, m), 1.44(2H, m), 1.53 (3H, t, J=7.1 Hz), 2.81 (1H, m), 3.25(3H, s), 4.2(2H, m), 4.63(2H, s), 7.2(1H, brs), 7.77–8.04(5H, m), 8.86(1H, s), 9.58(1H, d, J=7.3 Hz) FAB-MS m/z: 377(M+H)$^+$

Example 116

The following compound (Example 116) was synthesized by the same process as that in Example 47:

8-(3-Aminomethylphenyl)-1-cyclopropyl-9-methoxy-4-oxo-4H-quinolizine-3-carboxylic acid $^1$H-NMR(CF$_3$COOD) δ: 1.06–1.10(2H, m), 1.35–1.40 (2H, m), 3.01–3.08(1H, m), 3.75(3H, s), 4.63(2H, s), 7.78–7.86(2H, m), 8.04–8.11(3H, m), 8.62(1H, s), 9.42(1H, d, J=7.3 Hz) FAB-MS m/z: 365(M+H)$^+$

Example 117

The following compounds (Examples 117 to 120) were synthesized by the same process as that in Example 79:

1-Cyclopropyl-8-(3-dimethylaminomethylphenyl)-9-methyl-4-oxo-4H-quinolizine-3-carboxylic acid $^1$H-NMR(CF$_3$COOD) δ: 1.20–1.23(2H, m), 1.53–1.57 (2H, m), 2.79–2.85(1H, m), 3.24(6H, s), 3.29(3H, s), 4.69 (2H, s), 7.85–7.97(4H, m), 8.08(1H, d, J=7.1 Hz), 9.61(1H, d, J=6.6 Hz) FAB-MS m/z: 377(M+H)$^+$

Example 118

8-[3-(Tert-butylaminomethyl)phenyl]-1-cyclopropyl-9-methyl-4-oxo-4H-quinolizine-3-carboxylic acid $^1$H-NMR(CF$_3$COOD) δ: 1.20–1.23(2H, m), 1.53–1.58 (2H, m), 1.80(9H, s), 2.80–2.86(1H, m), 3.29(3H, s), 4.63 (2H, s), 7.78–7.90(4H, m), 8.07(1H, d, J=7.1 Hz), 8.87(1H, s), 9.60(1H, d, J=7.1 Hz) FAB-MS m/z: 406(M+H)$^+$

Example 119

1-Cyclopropyl-9-methyl-4-oxo-8-(3-piperazin-1-ylmethylphenyl)-4H-quinolizine-3-carboxylic acid $^1$H-NMR(CF$_3$COOD) δ: 1.20–1.23(2H, m), 1.55–1.57 (2H, m), 2.80–2.82(1H, m), 3.28(3H, s), 4.03–4.31(8H, m), 4.88(2H, s), 7.87–7.98(4H, m), 8.05(1H, d, J=7.3 Hz), 8.88(1H, s), 9.61(1H, d, J=7.3 Hz) FAB-MS m/z: 419(M+H)$^+$

Example 120

1-Cyclopropyl-8-(4-fluoro-5-methylaminomethylthiophen-2-yl)-9-methyl-4-oxo-4H-quinolizine-3-carboxylic acid $^1$H-NMR(CF$_3$COOD) δ: 1.15–1.16(2H, m), 1.52–1.56 (2H, m), 2.78–2.80(1H, m), 3.23(3H, s), 3.44(3H, s), 4.81 (2H, s), 7.52(1H, d, J=2.0 Hz), 7.87(1H, brs), 8.07(1H, d, J=5.8 Hz), 8.87(1H, s), 9.52(1H, d, J=6.4 Hz) FAB-MS m/z: 387(M+H)$^+$

Example 121

8-(3-Aminomethyl-4-methoxyphenyl)-1-cyclopropyl-9-methyl-4-oxo-4H-quinolizine-3-carboxylic acid was synthesized from 3-formyl-4-methoxyphenylboronic acid by the same process as that of Example 1 followed by the processes of Examples 15, 56, 58 and 79:

$^1$H-NMR(CF$_3$COOD) δ: 1.06(2H, m), 1.43(2H, m), 2.69 (1H, m), 3.19(3H, s), 4.12(3H, s), 4.57(2H, brs), 7.22(2H, brs), 7.35(1H, d, J=8.7 Hz), 7.59(1H, d, J=2.2 Hz), 7.73 (1H, dd, J=8.7 Hz, J=2.2 Hz), 7.94 (1H, d, J=7.3 Hz), 8.72(1H, s), 9.44(1H, d, J=7.3 Hz) FAB-MS m/z: 379(M+H)$^+$

Example 122

8-(4-Aminomethylphenyl)-1-cyclopropyl-7-fluoro-9-methyl-4-oxo-4H-quinolizine-3-carboxylic acid was synthesized from ethyl 8-chloro-1-cyclopropyl-7-fluoro-9-methyl-4-oxo-4H-quinolizine-3-carboxylate by the same process as that of Example 24:

$^1$H-NMR(CF$_3$COOD)[ ]: 1.13–1.18(2H, m), 1.48–1.53 (2H, m), 2.80(1H, m), 3.25(3H, s), 4.66(2H, s), 7.35(1H, br s), 7.54–7.70 (4H, m), 8.30(1H, s), 9.30–9.45(1H, m) FAB-MS m/z: 367(M+H)$^+$

Example 123

Ethyl 1-cyclopropyl-7-fluoro-9-methyl-4-oxo-8-{4-[(tritylamino)methyl]thiophen-2-yl}-4H-quinolizine-3-carboxylate was synthesized from ethyl 8-chloro-1-cyclopropyl-7-fluoro-9-methyl-4-oxo-4H-quinolizine-3-carboxylate by the same process as that of Example 1:

$^1$H-NMR(CDCl$_3$) δ: 0.73–0.77(2H, m), 1.02–1.07(2H, m), 1.43(3H, t, J=7.1 Hz), 2.32–2.38(1H, m), 2.99(3H, s), 3.40(2H, s), 4.38–4.45(2H, m), 7.20–7.60(17H, m), 8.35 (1H, s), 9.30–9.45(1H, m)

Example 124

8-(4-Aminomethylthiophen-2-yl)-1-cyclopropyl-7-fluoro-9-methyl-4-oxo-4H-quinolizine-3-carboxylic acid was synthesized from the compound of Example 123 by the same process as that of Example 47.

$^1$H-NMR(CF$_3$COOD) δ: 2.07–2.12(2H, m), 2.45–2.54 (2H, m), 3.70–3.79 (1H, m), 4.38(3H, s), 5.60(2H, s), 8.83–9.11(2H, m), 9.75(1H, s), 10.10(1H, m) FAB-MS m/z: 373(M+H)$^+$

The compounds of the present invention are antibacterial agents usable for the treatment of local infectious diseases or general infectious diseases of human beings or animals caused by Gram-positive bacteria, Gram-negative bacteria, anaerobic bacteria, acid-fast bacteria, etc. The compounds of the present invention are usable either alone or together with a pharmaceutically acceptable adjuvant, diluent, binder, etc. and in the form of a general medicinal composition such as tablets, sugar-coated tablets, capsules, injection, cream, ointment, liquid or powder. The compounds of the present invention are usable either alone or in the form of a mixture of two or more of them. The dose of them varies depending on the symptoms, age, body weight, etc. of the patient. Usually, they are administered to adults in a dose of 0.05 to 100 mg/kg/day, preferably 0.1 to 50 mg/kg/day, in the systemic administration. When they are used for the local treatment, the concentration of the active ingredient is 0.01 to 5%, preferably 0.1 to 3%.

The following formulations by no means limit the scope of the present invention.

Formulation Example 1

Tablets each comprising the following components were prepared by an ordinary method:

| | |
|---|---|
| Compound of Example 27 | 100 mg |
| Corn starch | 50 mg |
| Carboxymethylcellulose calcium | 25 mg |
| Crystalline cellulose | 20 mg |
| Magnesium stearate | 5 mg |
| Total | 200 mg |

The in vitro antibacterial activities of the compounds provided by the present invention were tested by a standard method of Chemotherapy Society of Japan, i.e. an agar plate dilution method disclosed in CHEMOTHERAPY Vol. 29, pages 76–79, 1981, and the activities of them on anaerobic bacteria were tested by a method disclosed in CHEMOTHERAPY Vol. 27, 559–590, 1979. The results were shown in terms of the minimum inhibition concentration (MIC, μg/ml) for the growth of the bacteria. The results are shown in Tables 1 to 5.

Levofloxacin was used as a comparative antibacterial agent. Levofloxacin is a widely prescribed, commercial quinolone antibacterial agent.

The structural formula of Levofloxacin is as follows:

TABLE 1

Antimicrobial spectrum MIC (μg/ml)

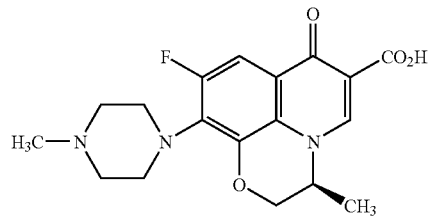

| Microorganism | Levofloxacin | Example 24 | Example 26 | Example 27 |
|---|---|---|---|---|
| Staphylococcus aureus IFO 13276 | 0.125 | 0.031 | 0.008 | ≦0.004 |
| Staphylococcus aureus JCM 2874 | 0.25 | 0.031 | 0.008 | ≦0.004 |
| Staphylococcus aureus IID 803(Smith) | 0.125 | 0.031 | 0.008 | ≦0.004 |
| Staphylococcus aureus Clin-211(MRSA) | 4 | 0.5 | 0.125 | 0.031 |
| Staphylococcus epidermidis IFO 12993 | 0.25 | 0.063 | 0.016 | 0.008 |
| Micrococcus luteus KI 3122 | 1 | 0.5 | 0.125 | 0.063 |
| Streptococcus pneumoniae IID 553 | 0.5 | 0.125 | 0.25 | 0.125 |
| Enterococcus faecalis RIMD 3116001 | 1 | 0.25 | 0.25 | 0.063 |
| Enterococcus faecalis CSJ 1212 | 0.5 | 0.25 | 0.125 | 0.031 |
| Bacillus subtilis JCM 2499 | 0.031 | 0.016 | ≦0.004 | ≦0.004 |
| Escherichia coli IFO 12734 | 0.031 | 0.063 | 0.125 | 0.063 |
| Klebsiella pneumoniae IID 865 | 0.008 | 0.008 | 0.008 | ≦0.004 |
| Pseudomonas aeruginosa CSJ 1853 | 0.5 | 0.5 | 0.25 | 0.25 |
| Branhamella catarrhalis IID 5233 | 0.031 | 0.063 | 0.016 | ≦0.004 |
| Haemophilus influenzae IID 984 | 0.016 | 0.016 | 0.016 | 0.008 |
| Bacteroides fragilis GAI 0675 | 0.5 | 0.25 | 0.125 | 0.031 |
| Bacteroides thetaiotaomicron ATCC 29741 | 4 | 0.5 | 0.25 | 0.125 |

TABLE 1-continued

Antimicrobial spectrum MIC (μg/ml)

[Chemical structure of a fluoroquinolone compound with F, CO₂H, methylpiperazine, and oxazine ring with CH₃ group]

| Microorganism | Levofloxacin | Example 24 | Example 26 | Example 27 |
|---|---|---|---|---|
| *Propionibacterium acnes* JCM 6425 | 0.25 | 0.125 | 0.063 | 0.031 |

TABLE 2

Antimicrobial spectrum MIC (μg/ml)

| Microorganism | Example 28 | Example 31 | Example 32 | Example 36 |
|---|---|---|---|---|
| *Staphylococcus aureus* IFO 13276 | 0.008 | 0.008 | 0.008 | 0.016 |
| *Staphylococcus aureus* JCM 2874 | 0.008 | 0.008 | 0.016 | 0.016 |
| *Staphylococcus aureus* IID 803(Smith) | 0.008 | 0.008 | 0.008 | 0.008 |
| *Staphylococcus aureus* Clin-211(MRSA) | 0.125 | 0.125 | 0.125 | 0.125 |
| *Staphylococcus epidermidis* IFO 12993 | 0.031 | 0.016 | 0.016 | 0.016 |
| *Micrococcus luteus* KI 3122 | 0.25 | 0.125 | 0.25 | 0.125 |
| *Streptococcus pneumoniae* IID 553 | 0.25 | 0.5 | 0.5 | 0.5 |
| *Enterococcus faecalis* RIMD 3116001 | 0.25 | 0.5 | 0.25 | 0.25 |
| *Enterococcus faecalis* CSJ 1212 | 0.125 | 0.25 | 0.125 | 0.25 |
| *Bacillus subtilis* JCM 2499 | ≦0.004 | ≦0.004 | ≦0.004 | ≦0.004 |
| *Escherichia coli* IFO 12734 | 0.25 | 0.125 | 0.25 | 0.25 |
| *Klebsiella pneumoniae* IID 865 | 0.031 | 0.031 | 0.016 | 0.031 |
| *Pseudomonos aeruginosa* CSJ 1853 | 2 | 0.5 | 1 | 0.5 |
| *Branhamella catarrhalis* IID 5233 | 0.031 | 0.031 | 0.031 | 0.031 |
| *Haemophilus influenzae* IID 984 | 0.25 | 0.125 | 0.063 | 0.063 |
| *Bacteroides fragilis* GAI 0675 | 0.125 | 0.25 | 0.063 | 0.125 |
| *Bacteroides thetaiotaomicron* ATCC 29741 | 0.25 | 1 | 0.25 | 0.5 |
| *Propionibacterium acnes* JCM 6425 | — | 0.25 | 0.008 | 0.063 |

TABLE 3

Antimicrobial spectrum MIC (μg/ml)

| Microorganism | Example 38 | Example 46 | Example 63 |
|---|---|---|---|
| *Staphylococcus aureus* IFO 13276 | 0.008 | ≦0.004 | 0.008 |
| *Staphylococcus aureus* JCM 2874 | ≦0.004 | ≦0.004 | 0.008 |
| *Staphylococcus aureus* IID 803(Smith) | ≦0.004 | ≦0.004 | 0.008 |
| *Staphylococcus aureus* Clin-211(MRSA) | 0.063 | 0.031 | 0.063 |
| *Staphylococcus epidermidis* IFO 12993 | 0.016 | (0.008) | (0.016) |
| *Micrococcus luteus* KI 3122 | 0.125 | 0.125 | 0.125 |

TABLE 3-continued

| Microorganism | Antimicrobial spectrum MIC (µg/ml) | | |
|---|---|---|---|
| | Example 38 | Example 46 | Example 63 |
| Streptococcus pneumoniae IID 553 | 0.125 | 0.125 | 1 |
| Enterococcus faecalis RIMD 3116001 | 0.125 | 0.063 | 1 |
| Enterococcus faecalis CSJ 1212 | 0.125 | 0.063 | 0.5 |
| Bacillus subtilis JCM 2499 | ≦0.004 | ≦0.004 | ≦0.004 |
| Escherichia coli IFO 12734 | 0.125 | 0.125 | 0.125 |
| Klebsiella pneumoniae IID 865 | 0.031 | 0.063 | 0.016 |
| Pseudomonos aeruginosa CSJ 1853 | 2 | 1 | 1 |
| Branhamella catarrhalis IID 5233 | 0.016 | 0.016 | 0.063 |
| Haemophilus influenzae IID 984 | 0.125 | (0.031) | (0.125) |
| Bacteroides fragilis GAI 0675 | 0.063 | 0.125 | 0.063 |
| Bacteroides thetaiotaomicron ATCC 29741 | 0.25 | 0.25 | 0.25 |
| Propionibacterium acnes JCM 6425 | — | 0.016 | 0.031 |

TABLE 4

| Microorganism | Antimicrobial spectrum MIC (µg/ml) | | | |
|---|---|---|---|---|
| | Example 117 | Example 119 | Example 89 | Example 121 |
| Staphylococcus aureus IFO 13276 | 0.063 | 0.063 | 0.031 | 0.016 |
| Staphylococcus aureus JCM 2874 | 0.125 | 0.063 | 0.063 | 0.016 |
| Staphylococcus aureus IID 803(Smith) | 0.063 | 0.063 | 0.063 | 0.016 |
| Staphylococcus aureus Clin-211(MRSA) | 1 | 1 | 0.5 | 0.25 |
| Staphylococcus epidermidis IFO 12993 | 0.125 | 0.125 | 0.125 | 0.031 |
| Micrococcus luteus KI 3122 | 1 | 1 | 0.5 | 0.125 |
| Streptococcus pneumoniae IID 553 | 0.5 | 0.5 | 0.5 | 0.031 |
| Enterococcus faecalis RIMD 3116001 | 1 | 1 | 0.5 | 0.063 |
| Enterococcus faecalis CSJ 1212 | 0.5 | 0.5 | 0.25 | 0.031 |
| Bacillus subtilis JCM 2499 | 0.031 | 0.016 | 0.016 | ≦0.004 |
| Escherichia coli IFO 12734 | 0.5 | 1 | 0.25 | 0.063 |
| Klebsiella pneumoniae IID 865 | 0.031 | 0.063 | 0.016 | ≦0.004 |
| Pseudomonos aeruginosa CSJ 1853 | 1 | 4 | 1 | 0.5 |
| Branhamella catarrhalis IID 5233 | 0.125 | 0.25 | 0.125 | 0.063 |
| Haemophilus influenzae IID 984 | 0.063 | 0.25 | 0.031 | 0.008 |
| Bacteroides fragilis GAI 0675 | 0.5 | 1 | 0.5 | 0.5 |
| Bacteroides thetaiotaomicron ATCC 29741 | 1 | 2 | 1 | 4 |
| Propionibacterium acnes JCM 6425 | 0.5 | 2 | 0.5 | 0.25 |

TABLE 5

| Antimicrobial spectrum MIC (μg/ml) | | | |
|---|---|---|---|
| Microorganism | Example 113 | Example 97 | Example 111 |
| Staphylococcus aureus IFO 13276 | 0.031 | 0.016 | 0.016 |
| Staphylococcus aureus JCM 2874 | 0.063 | ≦0.004 | 0.031 |
| Staphylococcus aureus IID 803(Smith) | — | ≦0.004 | 0.016 |
| Staphylococcus aureus Clin-211 (MRSA) | — | 0.063 | 0.25 |
| Staphylococcus epidermidis IFO 12993 | — | 0.016 | 0.031 |
| Micrococcus luteus KI 3122 | 0.25 | 0.125 | 0.25 |
| Streptococcus pneumoniae IID 553 | 0.5 | 0.25 | 0.125 |
| Enterococcus faecalis RIMD 3116001 | 0.5 | 0.25 | 0.125 |
| Enterococcus faecalis CSJ 1212 | 0.5 | 0.125 | 0.063 |
| Bacillus subtilis JCM 2499 | 0.016 | — | — |
| Escherichia coli IFO 12734 | 0.063 | 0.063 | 0.063 |
| Klebsiella pneumoniae IID 865 | 0.008 | 0.031 | 0.008 |
| Pseudomonos aeruginosa CSJ 1853 | 1 | 0.25 | 0.25 |
| Branhamella catarrhalis IID 5233 | 0.125 | 0.031 | 0.031 |
| Haemophilus influenzae IID 984 | 0.031 | 0.031 | 0.008 |
| Bacteroides fragilis GAI 0675 | 1 | 0.031 | 0.25 |
| Bacteroides thetaiotaomicron ATCC 29741 | 2 | 0.125 | 0.5 |
| Propionibacterium acnes JCM 6425 | — | 0.031 | 0.125 |

It is clear from the results shown in Tables 1 to 5 that new 4-oxoquinolizine antibacterial agents having a strong antibacterial effect on gram-positive bacteria, gram-negative bacteria or anaerobic bacteria can be provided by the present invention.

What is claimed is:

1. A compound having the following formula (I) or a pharmacologically acceptable salt thereof:

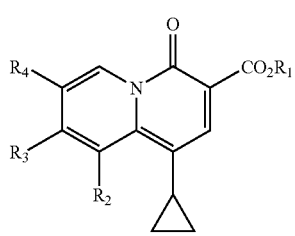

wherein:

$R_1$ represents a hydrogen atom or a carboxyl-protecting group, $R_2$ represents a hydrogen atom, a halogen atom, a lower alkyl group, a lower alkoxyl group or hydroxyl group, $R_3$ represents a thiophenyl or furyl group and $R_3$ has a substituent selected from the group consisting of a hydrogen atom, a lower alkyl group, a lower alkoxyl group, a nitro group, a cyano group, an amino group, a formyl group, an acetyl group, a carbamoyl group, a ureido group, a halogen atom, a hydroxyl group and a carboxyl group, and $R_4$ represents a hydrogen atom or a halogen atom.

2. The compound of claim 1 or the pharmacologically acceptable salt thereof, wherein in Formula (I), $R_4$ is a hydrogen atom or a fluorine atom.

3. The compound claim 1 or the pharmacologically acceptable salt thereof of, wherein in Formula (I), $R_1$ is a hydrogen atom.

4. An antibacterial composition comprising the compound of claim 1 or the pharmacologically acceptable salt thereof, as an active ingredient.

5. The antibacterial composition of claim 4, where in Formula (I), $R_4$ is a hydrogen atom or a fluorine atom.

6. The antibacterial composition of claim 4, wherein in Formula (I), $R_1$ is a hydrogen atom.

7. A method preparing a compound having the following formula (1):

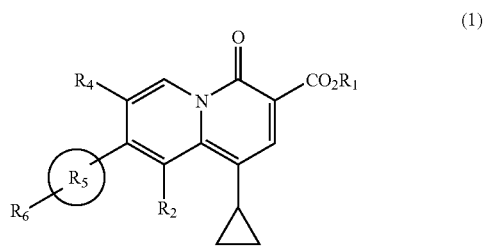

wherein:

$R_1$ represents a hydrogen atom or a carboxyl-protecting group, $R_2$ represents a hydrogen atom, a halogen atom, a lower alkyl group, a lower alkoxyl group or hydroxyl group, $R_4$ represents a hydrogen atom or a halogen atom.

$R_5$ represents a thiophenyl or furyl group, and $R_6$ represents a substituent selected from the group consisting of a hydrogen atom, a lower alkyl group, a lower alkoxyl group, a nitro group, a cyano group, an amino group, a formyl group, an acetyl group, a carbamoyl group, a ureido group, a halogen atom, a hydroxyl group and a carboxyl group, or the pharmacologically acceptable salt thereof, said method comprising reacting a compound (2) having the following formula (2):

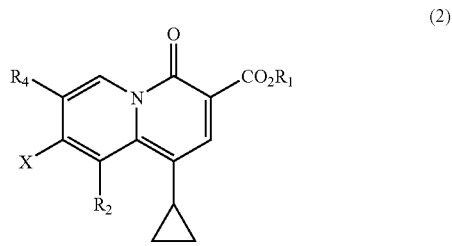

wherein:

$R_1$ represents a hydrogen atom or a carboxyl-protecting group, $R_2$ represents a hydrogen atom, a halogen atom, a lower alkyl group, a lower alkoxyl group or hydroxyl group, $R_4$ represents a hydrogen atom or a halogen atom, and X represents a halogen atom, with a compound having the following formula (3):

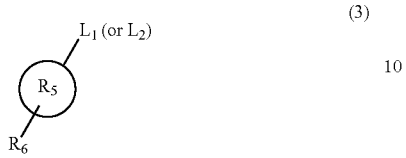

wherein:

$R_5$ represents a thiophenyl or furyl group;

$R_6$ represents a substituent selected from the group consisting of a hydrogen atom, a lower alkyl group, a lower alkoxyl group, a nitro group, a cyano group, an amino group, a formyl group, an acetyl group, a carbamoyl group, a ureido group, a halogen atom, a hydroxyl group and a carboxyl group, $L_1$ represents tin (alkyl group)$_2$, and $L_2$ represents boron (lower alkoxy group)$_2$.

8. The method of claim 7, wherein in Formula (I), $R_4$ is a hydrogen atom or a fluorine atom.

9. The method of claim 7, wherein Formula (I), $R_1$ is a hydrogen atom.

10. A method of preparing a compound having the following formula (1):

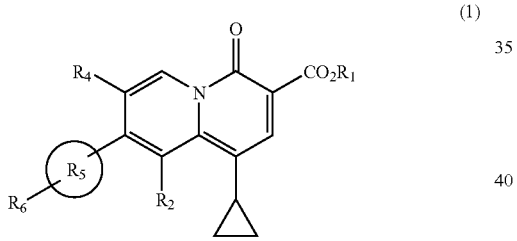

wherein:

$R_1$ represents a hydrogen atom or a carboxyl-protecting group, $R_2$ represents a hydrogen atom, a halogen atom, a lower alkyl group, a lower alkyl group, a lower alkoxyl group or hydroxyl group, $R_4$ represents a hydrogen atom or a halogen atom, $R_5$ represents a thiophenyl or furyl group, and $R_6$ represents a substituent selected from the group consisting of a hydrogen atom, a lower alkyl group, a lower alkoxyl group, a nitro group, a cyano group, an amino group, a formyl group, an acetyl group, a carbamoyl group, a ureido group, a halogen atom, a hydroxyl group and a carboxyl group, or the pharmacologically acceptable salt thereof, said method comprising reacting a compound (2) having the following formula (2):

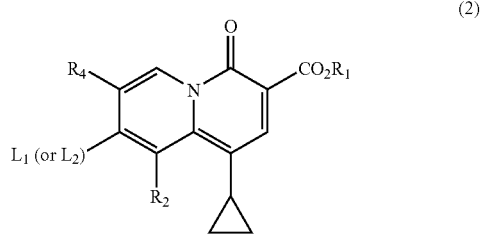

wherein:

$R_1$ represents a hydrogen atom or a carboxyl-protecting group, $R_2$ represents a hydrogen atom, a halogen atom, a lower alkyl group, a lower alkoxyl group or hydroxyl group, $R_4$ represents a hydrogen atom or a halogen atom.

$L_1$ represents tin (alkyl group)$_2$, and $L_2$ represents boron (lower alkoxy group)$_2$, with a compound having the following formula (3):

wherein:

$R_5$ represents a thiophenyl or furyl group, and $R_6$ represents a substituent selected from the group consisting of a hydrogen atom, a lower alkyl group, a lower alkoxyl group, a nitro group, a cyano group, an amino group, an acetyl group, a carbamoyl group, a ureido group, a halogen atom, a hydroxyl group and a carboxyl group, and X represents a halogen atom.

11. The method of claim 10, wherein in Formula (I), $R_4$ is a hydrogen atom or a fluorine atom.

12. The method of claim 10, wherein in Formula (I), $R_1$ is a hydrogen atom.

* * * * *

UNITED STATES PATENT AND TRADEMARK OFFICE
CERTIFICATE OF CORRECTION

| | |
|---|---|
| PATENT NO. | : 7,223,773 B2 |
| APPLICATION NO. | : 10/809874 |
| DATED | : May 29, 2007 |
| INVENTOR(S) | : Ryoichi Fukumoto et al. |

It is certified that error appears in the above-identified patent and that said Letters Patent is hereby corrected as shown below:

Title page, item (73) Assignee should read as follows: Sato Pharmaceutical Co., Ltd., Tokyo (JP)

Column 1, Line 6 should read: "cation number PCT/JP02/10103, filed Sep. 27, 2002. (status,"

Signed and Sealed this

Thirty-first Day of March, 2009

JOHN DOLL
*Acting Director of the United States Patent and Trademark Office*